(12) United States Patent
Tankovich

(10) Patent No.: US 11,484,361 B2
(45) Date of Patent: Nov. 1, 2022

(54) TIP FOR MULTIPLE BEAM TISSUE THERAPY

(71) Applicant: Nikolai Tankovich, San Diego, CA (US)

(72) Inventor: Nikolai Tankovich, San Diego, CA (US)

( * ) Notice: Subject to any disclaimer, the term of this patent is extended or adjusted under 35 U.S.C. 154(b) by 0 days.

(21) Appl. No.: 16/552,517

(22) Filed: Aug. 27, 2019

(65) Prior Publication Data

US 2021/0059753 A1    Mar. 4, 2021

(51) Int. Cl.
| | | |
|---|---|---|
| *A61B 18/22* | (2006.01) | |
| *A61B 18/20* | (2006.01) | |
| *A61B 5/00* | (2006.01) | |
| *A61B 18/18* | (2006.01) | |

(52) U.S. Cl.
CPC .............. *A61B 18/22* (2013.01); *A61B 5/441* (2013.01); *A61B 2018/1823* (2013.01); *A61B 2018/20355* (2017.05); *A61B 2018/2253* (2017.05); *A61B 2018/2255* (2013.01); *A61B 2018/2272* (2013.01); *A61B 2018/22853* (2017.05)

(58) Field of Classification Search
CPC . A61B 18/22; A61B 5/441; A61B 2018/2253; A61B 2018/1823; A61B 2018/22853; A61B 2018/20355
See application file for complete search history.

(56) References Cited

U.S. PATENT DOCUMENTS

| | | | |
|---|---|---|---|
| 5,807,379 A * | 9/1998 | L'Esperance, Jr. ........................ | A61F 9/00804 606/5 |
| 6,406,474 B1 | 6/2002 | Neuberger | |
| 8,251,982 B2 | 8/2012 | Zaghetto | |
| 8,444,562 B2 * | 5/2013 | Barthe ................... | A61B 8/469 600/439 |
| 10,675,481 B1 | 6/2020 | Tankovich | |
| 2002/0151878 A1 * | 10/2002 | Shimmick ............... | A61F 9/008 606/5 |
| 2003/0216719 A1 * | 11/2003 | Debenedictis ......... | A61B 18/20 606/10 |
| 2004/0039312 A1 * | 2/2004 | Hillstead .................. | A61N 7/02 601/2 |
| 2005/0049582 A1 | 3/2005 | DeBenedictis | |

(Continued)

FOREIGN PATENT DOCUMENTS

| | | |
|---|---|---|
| KR | 20080004451 A1 | 1/2008 |
| RU | 2113827 C1 | 6/1998 |

(Continued)

OTHER PUBLICATIONS

SH Price, "The Peltier Effect and Thermoelectric Cooling", Mar. 26, 2007, Physics 212 Web Project, pp. 1-2 (Year: 2007).*

(Continued)

*Primary Examiner* — Catherine M Voorhees
(74) *Attorney, Agent, or Firm* — TMB Law; Timothy M. Brown

(57) ABSTRACT

The invention provides a tip that permits therapeutic electromagnetic energy systems to deliver multiple beams of overlapping, partially overlapping, and non-overlapping electromagnetic energy in the treatment of tissue disorders and conditions. The tip finds use with laser systems, intense pulsed light systems, LED systems, radiofrequency systems, and microwave systems.

32 Claims, 14 Drawing Sheets

(56) References Cited

U.S. PATENT DOCUMENTS

| | | | |
|---|---|---|---|
| 2006/0004306 A1* | 1/2006 | Altshuler | A61H 39/002 601/3 |
| 2006/0084953 A1 | 4/2006 | Tankovich | |
| 2006/0095096 A1* | 5/2006 | DeBenedictis | A61B 18/203 607/88 |
| 2006/0161142 A1 | 7/2006 | Sierra | |
| 2007/0139950 A1* | 6/2007 | Easley | A61B 18/22 362/551 |
| 2007/0244526 A1 | 10/2007 | Zaghetto | |
| 2008/0132886 A1* | 6/2008 | Cohen | A61B 18/203 606/34 |
| 2009/0069741 A1 | 3/2009 | Altshuler | |
| 2009/0118720 A1* | 5/2009 | Black | A61B 18/203 606/9 |
| 2010/0082019 A1 | 4/2010 | Neev | |
| 2012/0209257 A1* | 8/2012 | van der Weide | A61B 18/1815 606/23 |
| 2013/0096546 A1 | 4/2013 | Mirkov | |
| 2013/0103017 A1* | 4/2013 | Weckwerth | A61B 18/203 606/9 |
| 2014/0058227 A1* | 2/2014 | Yamanaka | G01N 21/64 600/316 |
| 2015/0051593 A1* | 2/2015 | Johnson | A61N 5/0616 606/9 |
| 2018/0296269 A1* | 10/2018 | Bhawalkar | A61B 18/203 |
| 2019/0025212 A1 | 1/2019 | Evans | |

FOREIGN PATENT DOCUMENTS

| | | |
|---|---|---|
| RU | 107931 B2 | 9/2011 |
| RU | 110265 B2 | 11/2011 |
| RU | 120008 U1 | 10/2012 |
| RU | 137201 U1 | 9/2013 |
| WO | 2006031632 A2 | 3/2006 |

OTHER PUBLICATIONS

Copending U.S. Appl. No. 16/546,267; Laser System for Multiple Beam Tissue Therapy; filed Aug. 20, 2019.
Extended European Search Report for copending EU Application No. 201931458 dated Jan. 20, 2021.
Extended European Search Report for copending EU Application No. 192077022 dated May 12, 2020.
Office Action for Copending S. Korea Application No. 10-2019-0170728, dated Mar. 31, 2021.
Office Action for Copending Russia Application No. 2020127609, dated Feb. 16, 2021.

* cited by examiner

TIP FOR MULTIPLE BEAM TISSUE THERAPY

FIELD OF THE INVENTION

The invention relates to a tip for use with therapeutic electromagnetic energy emitting systems and its use and manufacture in tissue therapy.

BACKGROUND OF THE INVENTION

Tips are attachable and detachable to laser and other energy source devices. Tips can be a part of a laser handpiece or other energy emitting system. Tips can be permanent and not a removable portion of the system. Tips can be disposable or reusable units.

Laser diodes are light sources where a direct current is applied to a semiconductor and electrical energy is transformed into laser light energy. The light is monochrome, and coherent with high directionality. Laser diodes typically emit in a continuous wave mode or with relative long pulses of hundreds of microseconds or more. Light power could be up to dozens of watts from one diode. Individual diodes can be assembled together to produce more power.

Solid state lasers use solid crystals as an active medium and a flash lamp or laser diodes as a pump source. The laser pulse duration in solid state lasers could be from a dozen femtoseconds to several seconds or a continuous wave. Laser energy could be from a fraction of miljoules up to dozens of Joules.

Some wavelengths of laser energy are preferentially absorbed in a particular type of tissue when the tissue contains a particular chromophore that has a peak or relatively high absorption at the particular wavelength. After being absorbed in the tissue, laser energy transforms into thermal energy and results in a rise of temperature. Use of a laser beam matched to a peak or relatively high absorption in tissue to treat the tissue is referred to as "selective photothermolysis." Photothermolysis is a decomposition by temperature rise caused by light. Some wavelengths are absorbed relatively uniformly in tissue and when these wavelengths are used to treat the tissue it is referred to as "non-selective photo thermolysis" or "homogeneous photothermolysis." The choice of wavelengths is important when these lasers are used in medicine and surgery, tattoo removal, skin peeling, and hair removal. Absorption in blood is lowest in a wavelength range between about 700 nm and about 1,300 nm with peaks at 1,450 nm and 1,940 nm. Absorption in Caucasian skin is lowest in a wavelength range between about 1,050 nm and about 1,150 and peaks in a wavelength of about 1,480, as well as at 1,930 nm.

In some medical laser applications, living tissue is intentionally modified or damaged with laser energy. Modification of tissue depends on the volumetric laser energy deposition and pulse duration. In typical cases, if the laser pulse is longer than several dozens of microseconds the typical result is a temperature increase in the skin tissue caused by the energy of the laser beam being absorbed in the blood vessels, the blood in the vessels, and the skin tissue. Temperature increase leads to tissue coagulation. In some cases, tissue adjacent the target tissue can also be damaged. There exists, for normal skin tissue, a skin tissue damage temperature threshold. Temperatures below the threshold produce no significant damage. The threshold depends on time and temperature. For periods of time (for example, between a few milliseconds and about one second) the damage to blood and blood vessels, the damage threshold is about 44°. For shorter laser pulses, such as a few microseconds, the threshold is in the range of about 66° to 72° C.

If the laser pulse is very short (typically between several nanoseconds [10-9 seconds] and one microsecond [10-6 seconds]) the tissue may be damaged due to explosion or evaporation in the area of laser absorption. The laser energy is absorbed by skin tissue, however laser pulse duration is very short and there is not enough time for the tissue to expand or for the heat to spread out of the laser spot. In these conditions, the tissue is mechanically ruptured in the region of laser absorption. For pulse durations longer than about 1 microsecond, the laser-tissue interactions are thermal. For pulses shorter than 1 microsecond, the effects tend to be mechanical in the form of ablation or tissue disruption.

Electromagnetic radiation emitting devices may not be lasers or laser systems but emit non-coherent radiation like intense pulsed light (IPL), microwave, ultrasonic, LED (light emitting diode) or a combination thereof.

IPL is a broadband source of electromagnetic radiation in near ultraviolet, visible, and near infrared spectrum. The source of IPL is a bulb filled with gas, like xenon, krypton or others, and two electrodes. A pulse of very high voltage (tens of kilovolts) is used to initiate a discharge current between electrodes. Then, initial discharge on the main discharge of electrical energy stored in the capacitor releases in the bulb. The high energy electrical pulse excites gas atoms in the bulb and produce spontaneous light emission. The pulse duration of IPL can be from microseconds to seconds, and have an energy from fractions to hundreds of Joules.

Microwave is electromagnetic radiation in the range of 300 MHz to 300 GHz. Microwave energy is produced in a magnetron (a vacuum tube where a stream of electrons interacts with a magnetic field in open metal cavities). Microwave radiation around 2.45 GHz is absorbed by water molecules in biological tissue and can heat the tissue. Microwave can be transmitted via antennas or waveguides and can be designed to focus microwave in a selected area of treatment.

Ultrasound is not electromagnetic radiation, but stress or compression mechanical waves in a media. The frequency of ultrasound wave is above 20 kHz. Generation of ultrasound waves for medical applications is mostly based on the piezoelectric effect, where oscillating electrical voltage applied to a transducer produces oscillating changes in the transducer's shape and stress waves. For medical applications, the ultrasound is mainly used for diagnostics, but if focused it can be used for disintegrating the tissue, for example distraction of certain tissues based on their properties or cutting.

What is needed in the art is an accessory for therapeutic electromagnetic systems that can permit the systems to simultaneously treat different layers of tissue with varying penetration and thermal effects of electromagnetic energy.

SUMMARY OF THE INVENTION

The invention provides a tip for use with therapeutic electromagnetic systems that permits the systems to simultaneously deliver multiple, overlapping beams of electromagnetic energy. The tip finds use with a variety of therapeutic electromagnetic systems such as laser, IPL, microwave, and ultraviolet systems.

BRIEF DESCRIPTION OF THE DRAWINGS

FIG. 5A shows the top view of the fractional window of FIG. 5.

Figure 1:
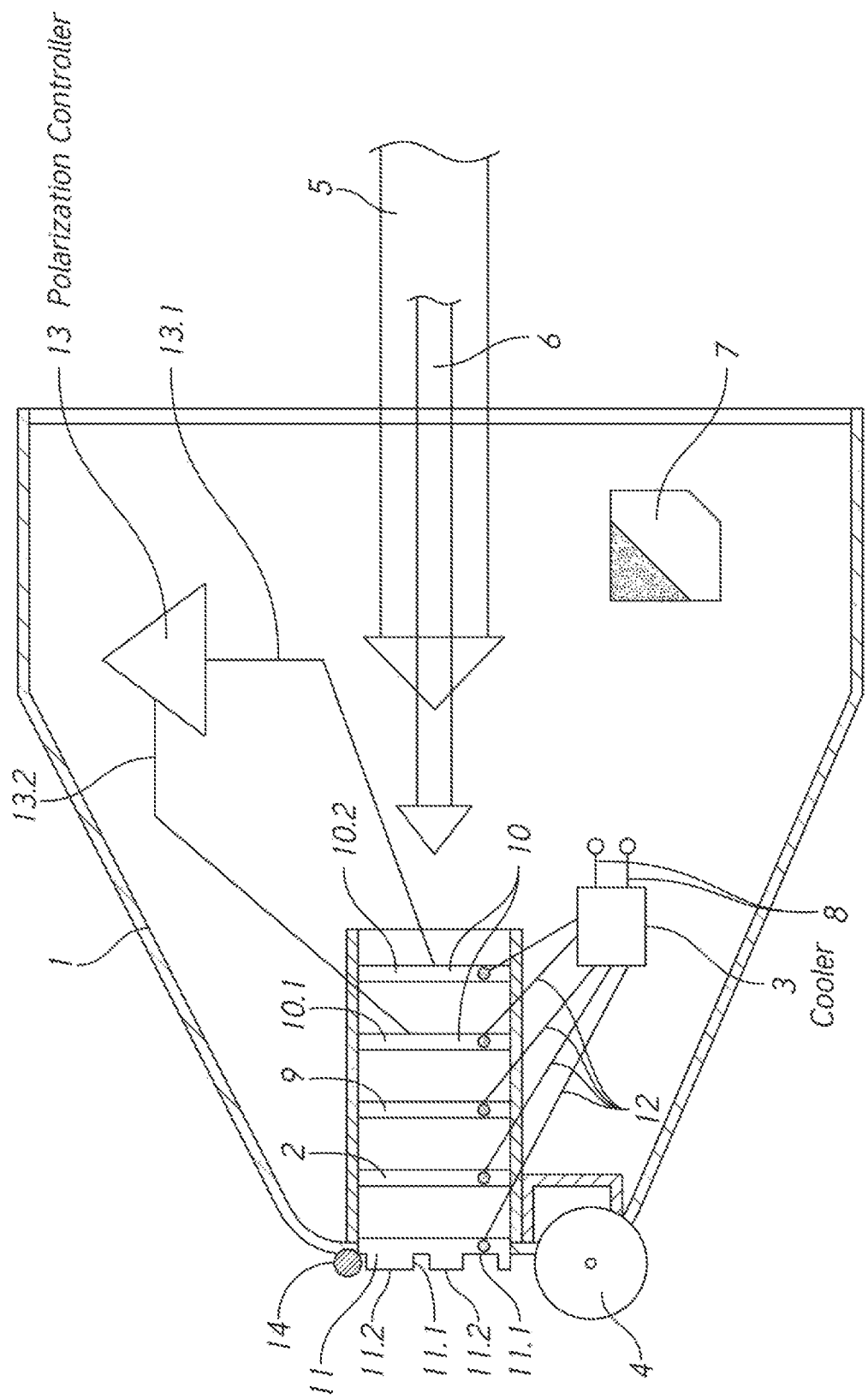
FIG. 1 is a drawing of a first embodiment of a tip of the invention.

Similar reference numbers denote corresponding features consistently throughout this specification and the attached drawings. While the drawings are presented to aid in the understanding of the invention, it will be understood that the present invention is not limited to what is disclosed in the drawings.

REFERENCE NUMBERS

1—Tip
2—Transmitting window
2.1—Coating for transmitting electromagnetic beam 5
2.2—Coating for transmitting electromagnetic beam 6
3—Thermoelectric cooler
4—Roller
5—Electromagnetic beam
6—Electromagnetic beam
7—Microchip
8—Microchip connectors
9—Transmitting window
9.1—Coating for transmitting electromagnetic beam 5
9.2—Coating for transmitting electromagnetic beam 6
10—Polarizing window
10.1—Window for polarizing electromagnetic beam 5
10.2—Window for polarizing electromagnetic beam 6
11—Fractional window
11.1—Fractional depression
11.2—Planar surface
12—Cooling connectors
13—Polarization controller
13.1—Nematic liquid crystal cell
13.2—Nematic liquid crystal cell
14—Contact sensor
15—Laser unit
16—Power supply
17—Conducting wire
18—Magnetron
19—Microwave conductor
20—Microwave
21—IPL source
22—Fiber optic conductor
23—Non-coherent light
24—Ultrasound transducer
25—Epidermis
26—Dermis
27—Skin lesion
29—Blocking coating
30—Shielded region
31—Beam separation window
32—Central opening
34—Beam separation coating
36—Split beams
38—Magnet
39—Magnetic field sensor
40—Display screen
41—Scanning mirror for electromagnetic beam 5
42—Scanning mirror for electromagnetic beam 6
43—Laser emission unit for electromagnetic beam 5
44—Laser emission unit for electromagnetic beam 6
51—Shielding window

DEFINITIONS

As used herein, the term "about" means the quantity, level, value, number, frequency, percentage, dimension, size, amount, weight or length that is referenced, or that varies (plus or minus) by as much as 30%, 25%, 20%, 15%, 10%, 9%, 8%, 7%, 6%, 5%, 4%, 3%, 2% or 1% of the referenced quantity, level, value, number, frequency, percentage, dimension, size, amount, weight or length.

As used herein, the phrase "skin condition" includes, but is not necessarily limited to, wrinkles, loss of elasticity, skin photoaging, scars, rhytides, acne, telangiectasia, vitiligo, skin lesions, tattoo removal, blepharoptosis, and combinations thereof.

As used herein, the phrase "skin lesion" refers to a disorder, condition, or injury affecting the skin. The phrase can refer to, without limitation, benign growths and lesions (e.g. actinic keratosis), neoplastic lesions (e.g. melanoma, basal cell carcinoma, and squamous cell carcinoma), burns and other wounds (e.g. post operational wounds), diabetic ulcers, and bed sores.

As used herein, the phrase "electromagnetic energy" includes, but is not necessarily limited to, laser energy, coherent and non-coherent light energy, microwave energy, ultraviolet energy, radiofrequency energy, and IPL energy.

As used herein, the phrase "electromagnetic beam" includes, but is not necessarily limited to, laser beams, coherent and non-coherent light beams, microwave energy beams, ultraviolet energy beams, radiofrequency beams, and IPL beams.

As used herein, the terms "treat," "treating," and "treatment" refer to the clinical intervention of a disease or condition in an attempt to alter, alleviate, ameliorate, prevent, lessen, or reverse the progression or symptoms of the disease or condition.

DETAILED DESCRIPTION

In at least one aspect, the invention provides a tip for use with electromagnetic energy emitting systems in tissue treatment. The tip can be adapted to be detachably connected to, or manufactured as an integral part of, electromagnetic energy emitting systems to permit the systems to emit two or more beams of electromagnetic energy simultaneously with complete overlap, partial overlap, or non-overlap of the beams on the treated tissue. The tip can be used with beams of electromagnetic energy having the same or different wavelengths and modes.

Electromagnetic energy emitting systems for use with the tip include systems that emit electromagnetic energy capable of treating a tissue disorder or condition in a patient. Suitable electromagnetic energy emitting systems include, but are not limited to, laser systems, coherent light systems, non-coherent light systems, intense pulsed light (IPL) systems, light emitting diode (LED) systems, microwave systems, or combinations thereof. In one non-limiting aspect of the invention, the electromagnetic emitting system comprises an IPL light source. The IPL light source can have a pulse duration of seconds to microseconds and an energy of a faction of Joules to hundreds of Joules. The electromagnetic emitting system can include a module or system adapted to administer ultrasound energy to the tissue of a patient.

Laser systems suitable for use with the tip include, but are not limited to, solid-state lasers, laser diode lasers, gas lasers, chemical lasers, dye lasers, metal-vapor lasers, semiconductor lasers, or combinations thereof. The laser system can be a dermatological laser, ophthalmic laser, surgical laser, or cosmetic laser. The laser system can contain least one of a $CO_2$ laser and a solid state Er: YSSG laser. In at least one aspect of the invention, the laser system comprises two or more laser diodes. Laser diodes for use with the tip can have a power of one dozen, two dozen, three dozen, four dozen, five dozen, six dozen, seven dozen or more watts. In other aspects, the laser system comprises one or more solid state lasers. The solid state lasers can have a pulse that lasts from a dozen femtoseconds to several seconds, or the solid state lasers can deliver energy in a continuous wave. The solid state laser energy can range between a fraction of a millijoule and dozens of Joules.

The tip can be used with laser systems that emit two or more laser beams having the same or different wavelengths. The wavelengths can be about 540 nm, about 700 nm, about 980 nm, about 1,064 nm, about 1,440 nm, about 1,300 nm, about 1,450 nm, about 1,550 nm, about 1,930 nm, about 2,790 nm, about 2,790 nm, about 2,940 nm, about 10,600 nm, about 1,550 nm, or about 2,790 nm. In some aspects of the invention, the laser system emits one or more laser beams having a wavelength of 1,550 nm and one or more laser beams having a wavelength of 2,790 nm. The tip can be used with lasers that emit two or more laser beams simultaneously in the same or different modes. The laser beams can have a mode that is a continuous beam mode, a pulse beam mode, or a combination thereof. The laser beam mode can be at least hundreds of microseconds.

In some aspects of the invention, the tip is adapted to provide electromagnetic energy in addition to the electromagnetic energy produced by the electromagnetic energy emitting system. For example, the tip can have a module or system that emits coherent light, non-coherent light, ultrasound, microwave energy, or combinations thereof.

In at least one aspect of the invention, the length of the tip is a length that permits the tip to function as a standoff wherein the end of the tip is in the same plane as the focal point of the electromagnetic energy emitted from the electromagnetic energy emitting system that is attached to the tip.

In at least one aspect of the invention, the tip comprises at least one transmitting window that transmits beams of electromagnetic energy from the electromagnetic energy emitting system. The tip can contain one, two, three, four, five, or more transmitting windows. The transmitting windows have opposing planar surfaces and can be translucent and made of a material such as sapphire or thermoconductive glass. The transmitting windows can be beam shaping lenses that focus or shape the beams of electromagnetic energy on the tissue that is being treated, such as the skin of a patient, for example. The planar surfaces of the transmitting windows can be flat, concave, convex, or combinations thereof.

The surface of the transmitting windows can be coated with one or more layers of an antireflective coating that enhances the transmission of a selected one or more wavelengths of electromagnetic energy through the transmitting windows. The antireflective coatings can be on one or both planar surfaces of the transmitting windows. For example, the transmitting windows can have a first antireflective coating that enhances the transmission of a first one or more wavelengths of electromagnetic energy through the transmitting windows, and a second antireflective coating that enhances the transmission of a second one or more wavelengths of electromagnetic energy through the transmitting windows. The coatings can permit the wavelengths of electromagnetic energy to overlap on the tissue to which the electromagnetic energy is applied, such as the skin of a patient, for example. Suitable materials for the antireflective coatings include, but are not necessarily limited to, magnesium fluoride, yttrium oxide, silica oxide, aluminum oxide, cerium fluoride, hafnium fluoride, or combinations thereof. In some aspects of the invention, the coatings comprise a layer of one material having a low index of reflection, and a layer of a second material having a high index of reflection. For example, the coating can comprise a layer of magnesium fluoride, silica oxide, or cerium fluoride each having a low index of reflection, and a second layer of yttrium oxide, aluminum oxide, or hafnium fluoride each having a high index of reflection. Non-limiting examples of coating combinations include: magnesium fluoride and yttrium oxide; silica oxide and aluminum oxide; and cerium fluoride and hafnium fluoride. The antireflective coatings can have a thickness ranging between about 100 nanometers and about 500 nanometers.

In at least one aspect of the invention, the antireflective coatings can enhance the transmission of at least one wavelength of laser light through the laser transmitting windows. For example, the transmitting windows can have a first antireflective coating that enhances the transmission of a first one or more wavelengths of laser light, and a second antireflective coating that enhances the transmission of a second one or more wavelengths of laser light. The antireflective coatings can enhance the transmission of laser beams having a wavelength of about 540 nm, about 700 nm, about 980 nm, about 1,064 nm, about 1440 nm, about 1300 nm, about 1450 nm, about 1550 nm, about 1930 nm, about 2790 nm, about 2790 nm, about 2940 nm, or about 10600 nm.

In at least one aspect of the invention, the tip has one or more fractional windows having a pair of opposing planar surfaces. The fractional windows can be made of optical glass, optical quartz, or sapphire. At least one of the planar surfaces has one or more fractional depressions with one or more intervening planar lands. The fractional depressions can have the same or different shape. The fractional depressions can be in the shape of cylindrical columns. In some aspects, the fractional depressions form one or more depressed concentric rings on the outward facing surface of the fractional window. The fractional depressions scatter, absorb and/or reflect electromagnetic energy as it is emitted from an electromagnetic emitting system, while the planar lands transmit the electromagnetic energy without scattering, absorbing, reflecting, or otherwise modifying the electromagnetic energy. Thus, the depressions can fractionate a beam of electromagnetic energy into multiple fractions of electromagnetic energy having the same or different size and shape. The depressions can be arranged to fractionate the beams into multiple fractions of beams, wherein the fractionated beams are at least one of overlapping, partially overlapping, and non-overlapping beams. In at least one aspect of the invention, the fractional depressions fractionate laser light. The tip can comprise a plurality of fractional windows arranged in series with the fractional windows' planar surfaces opposing one another. The fractional windows can be located on the end of the tip, or they may be held within the tip body between the tip's transmitting windows. In some aspects of the invention, a fractional coating on the outward surface of the fractional window is substituted for the fractional depressions. The fractional coating provides the same function as the fractional depressions, and can be present in one or more layers. The fractional coating can be a non-translucent material that absorbs or reflects laser light. Suitable materials for the fractional coating include, but are not limited to, evaporated metal films (e.g. aluminum and gold), silica, scandium oxide, or combinations thereof. The fractional coating can be arranged in interchanging layers of these materials. In at least one aspect, the fractional coating comprises a layer of silica and a layer of scandium oxide. In other aspects, the fractional coating comprises two or more layers of an evaporated metal film. The fractional coating can have a thickness ranging between about 100 nanometers and about 500 nanometers.

First Embodiment

FIG. 1 depicts a first embodiment of the tip of the invention. Tip 1 is enclosed in a housing made of a suitable material, such as medical grade plastic which can be translucent or opaque. Tip 1 features transmitting window 2 and transmitting window 9 which are held in series within a column body. The column body can be made of the same or a similar material as the laser tip housing. Tip 1 is adapted to transmit electromagnetic beam 5 and electromagnetic beam 6 onto a treated tissue, such as the skin of a patient, for example. Transmitting window 2 and transmitting window 9 can feature antireflective coatings to enhance the simultaneous transmission of electromagnetic beam 5 and electromagnetic beam 6 through the transmitting windows such that the beams overlap on a treated surface. Transmitting window 2 and transmitting window 9 can be made of sapphire, thermoconductive glass, or other similar material suitable for transmitting light, such as laser light. In at least one aspect of the invention, electromagnetic beam 5 and electromagnetic beam 6 are laser beams emitted from a laser system attached to tip 1. The beams can be of the same or different wavelengths and can be of the same or different modes (e.g. continuous and pulse laser beams).

Tip 1 further features at least one polarizing window 10 adapted to polarize at least one of electromagnetic beam 5 and electromagnetic beam 6. Polarizing windows 10 can achieve polarization through polarizing coatings 10.1 and 10.2 on the planar surfaces of polarizing windows 10. In some aspects of the invention, polarizing windows 10 have nematic liquid crystal cells 13.1 and 13.2 in electronic communication with polarization controller 13. The polarization state and the transparency of window 10 can thus be controlled by electrical signals from polarization controller 13 which change the voltage of nematic liquid crystal cells 13.1 and 13.2. Thus, polarization controller 13 can be adapted to modulate at least one of electromagnetic beam 5 and electromagnetic beam 6 to produce a temporal shape of the beams making the leading edge of the beams more intense and the remaining pulse less intense to achieve thermal post conditioning. Alternatively, polarization controller 13 can be adapted to shape at least one of electromagnetic beam 5 and electromagnetic beam 6 such that the beginning of the pulses starts at a low intensity to achieve pre-heating, and the end of the pulses finish with a more intense energy. Polarizing windows 10 can be beam shaping lenses that focus or shape the electromagnetic energy on the tissue that is treated.

Tip 1 can contain fractional window 11. Fractional window 11 can be made from optical glass, silica or sapphire. Fractional window 11 can have one or more fractional depressions 11.1 surrounded by one or more planar lands 11.2 on the outward facing surface of fractional window 11. Fractional depressions 11.1 can have the same or similar shape, and can be in the shape of concentrically arranged cylindrical columns in at least one aspect of the invention. Fractional depressions 11.1 can scatter, absorb and/or reflect electromagnetic beam 5 and electromagnetic beam 6 thereby fractionating the beams into multiple fractions of electromagnetic energy having a modified size and shape. Thus, fractional depressions 11.1 can split one or both of electromagnetic beam 5 and electromagnetic beam 6 into a plurality of fractional electromagnetic beams having the same or different size and shape. Planar lands 11.2 of fractional window 11 transmit electromagnetic beam 5 and electromagnetic beam 6 without modification of the beams. In some aspects of the invention, a fractional coating on fractional window 11 is substituted for fractional depressions 11.1. The fractional coating achieves the same function as fractional depressions 11.1 and can be made from a non-translucent material that absorbs or reflects electromagnetic energy, such as laser light for example. Suitable materials for the fractional coating include evaporated metal films (e.g. aluminum and gold), silica, scandium oxide, magnesium fluoride, hafnium fluoride, or combinations thereof. The materials can be arranged in interchanging layers. In at least one aspect, the fractional coating comprises a layer of silica and a layer of scandium oxide. In other aspects, the fractional coating comprises a layer of magnesium fluoride and a layer of hafnium fluoride. The fractional coating can have a thickness between about 100 nanometers and about 500 nanometers.

Laser tip 1 contains roller 4 which is in electronic communication with microchip 7 such that when the tip is moved on a surface, such as the skin of a patient, roller 4 detects the rotation and provides a signal to microchip 7 resulting in microchip 7 instructing the electromagnetic energy system to emit electromagnetic beam 5 and electromagnetic beam 6.

In some aspects of the invention, tip 1 contains contact sensor 14 in communication with microchip 7 such that when contact sensor 14 is in contact with a surface, such as the skin of a patient, microchip 7 enables the electromagnetic energy emitting system to emit electromagnetic beam 5 and electromagnetic beam 6. That is, contact sensor 14 can act as safety that prevents the electromagnetic energy emitting system from emitting electromagnetic beams until the tip is in contact with the tissue that is to be treated.

Tip 1 can comprise thermoelectric cooler 3 which is in thermal communication with at least one of transmitting window 2, transmitting window 9, and polarizing window 10 through cooling connectors 12. Thermoelectric cooler 3 is in electronic communication with microchip 7 by microchip connectors 8 such that microchip 7 can control the temperature of at least one of transmitting window 2, laser transmitting window 9, and polarizing window 10 by activating and inactivating thermoelectric cooler 3 to maintain a predetermined temperature or temperature range thereby providing cooling so that tip 1 can treat the tissue of a patient without discomfort or damage to the tissue. Thermoelectric cooler 3 can be a Peltier cooling module.

Second Embodiment

Figure 2:
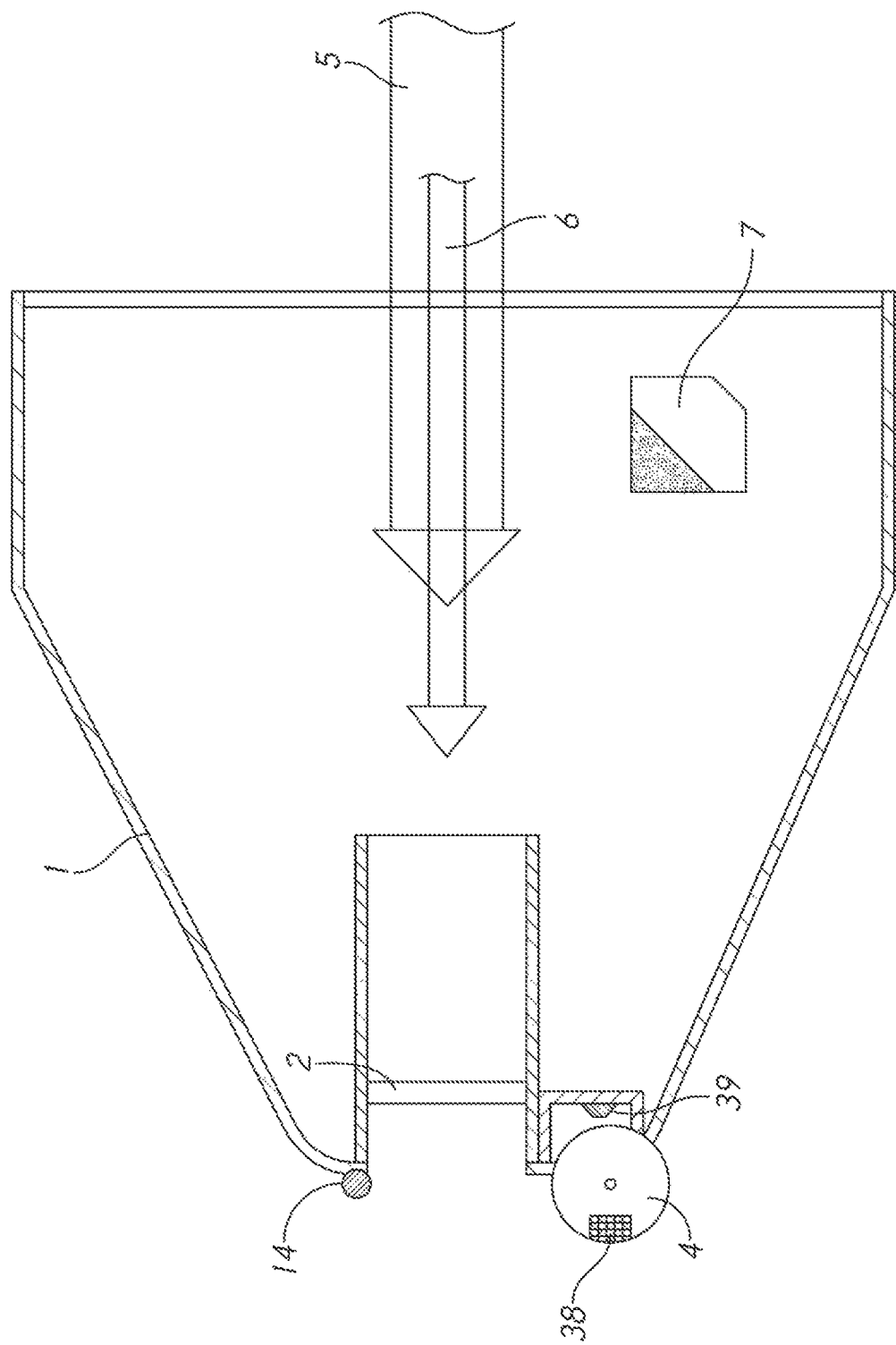
FIG. 2 is a drawing of a second embodiment of a tip of the invention having a single transmitting window.

FIG. 2 depicts a second embodiment of the tip of the invention. As with other the other embodiments of the tip, tip 1 is enclosed in a housing made of a suitable material, such as medical grade plastic which can be translucent or opaque. Tip 1 can have a single transmitting window 2 having one or more coatings selected to simultaneously transmit electromagnetic beam 5 and electromagnetic beam 6. Electromagnetic beam 5 and electromagnetic beam 6 can be of the same or different wavelengths. For example, transmitting window 2 can have a coating on one surface that enhances the transmission of electromagnetic beam 5 having a first wavelength, and a coating on the opposing surface that enhances the transmission of electromagnetic beam 6 having a second wavelength. The coatings can be on the planar surfaces of laser window 2. In at least one aspect of the invention, electromagnetic beam 5 and electromagnetic beam 6 are laser beams and the coatings are coatings that reduce reflection of the wavelengths by transmitting window 2.

The second embodiment of the tip can feature roller 4 having at least one magnet 38 on its surface or within the body of roller 4. Roller 4 is adapted to rotate as tip 1 is contacted with and moved across the skin of a patient. The rotation of roller 4 causes a periodic change in the magnetic field of magnets 38 which is detected by magnetic field sensor 39. Magnetic field sensor 39 then sends a signal to microchip 7 causing microchip 7 to activate an electromagnetic energy emitting system attached to laser tip 1 to emit electromagnetic beam 5 and electromagnetic beam 6. Tip 1 also features contact sensor 14 in communication with microchip 7 which acts as a safety to prevent an attached electromagnetic energy emitting system from emitting electromagnetic beam 5 and electromagnetic beam 6 until the tip is in contact with a surface that is to be treated, as disclosed herein.

Third Embodiment

Figure 3:
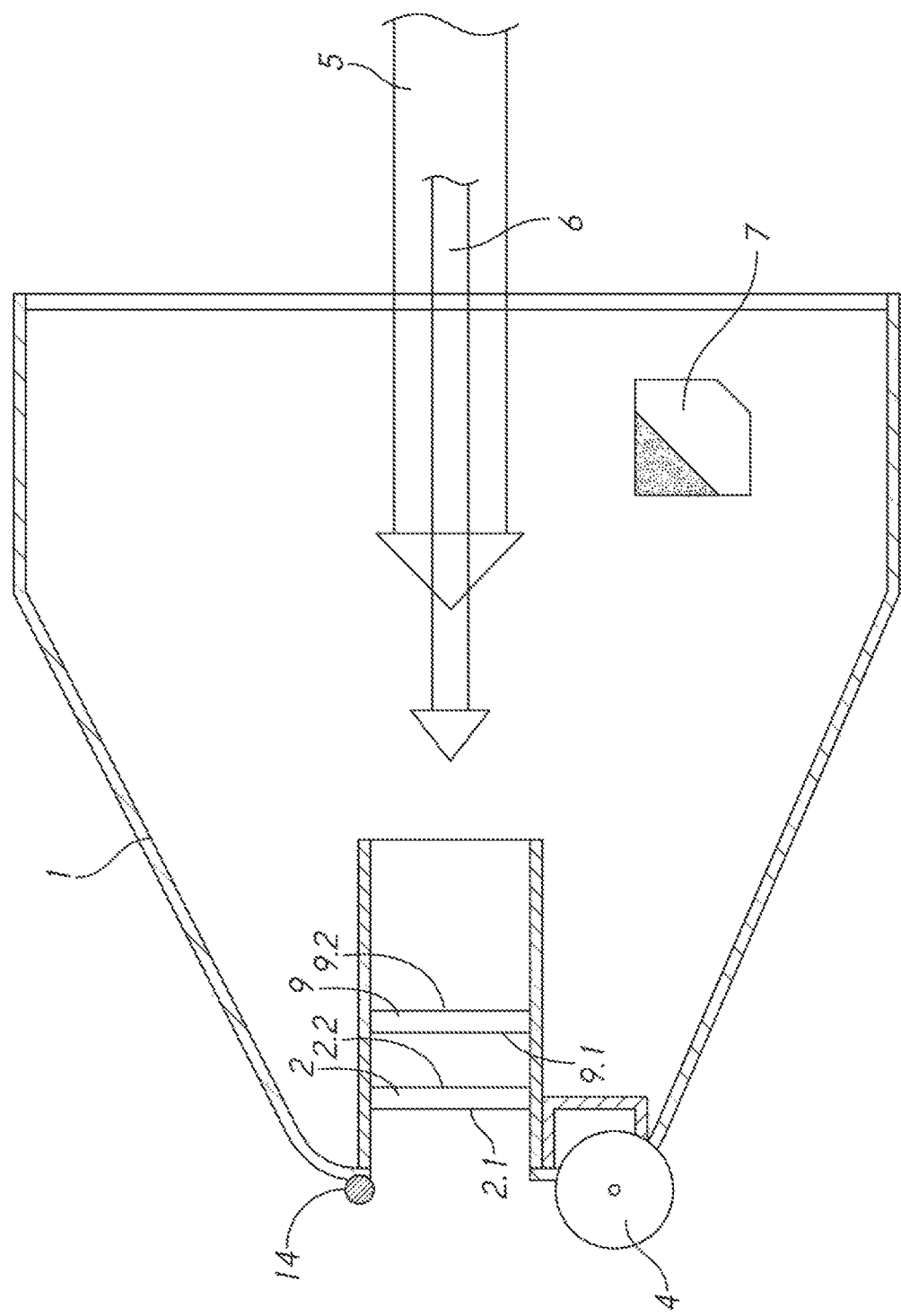
FIG. 3 is a drawing of a third embodiment of the tip of the invention having a pair of transmitting windows.

FIG. 3 depicts a third embodiment of the tip of the invention. In this embodiment, tip 1 can feature transmitting window 2 and transmitting window 9 having coatings 2.1, 2.2, 9.1, and 9.2 on the opposing planar surfaces of the transmitting windows. The coatings are adapted to simultaneously transmit electromagnetic beam 5 and electromagnetic beam 6. The electromagnetic beams can be of the same or different wavelengths. Coatings 2.1 and 9.1 can be adapted to transmit electromagnetic beam 5 having a first wavelength, while coatings 2.2 and 9.2 can be adapted to transmit electromagnetic beam 6 having a second wavelength. In at least one aspect, electromagnetic beam 5 and electromagnetic beam 6 are laser beams. The embodiment of FIG. 3 features roller 4 and contact sensor 14 which are in communication with microchip 7 as disclosed herein.

Fourth Embodiment

Figure 4:
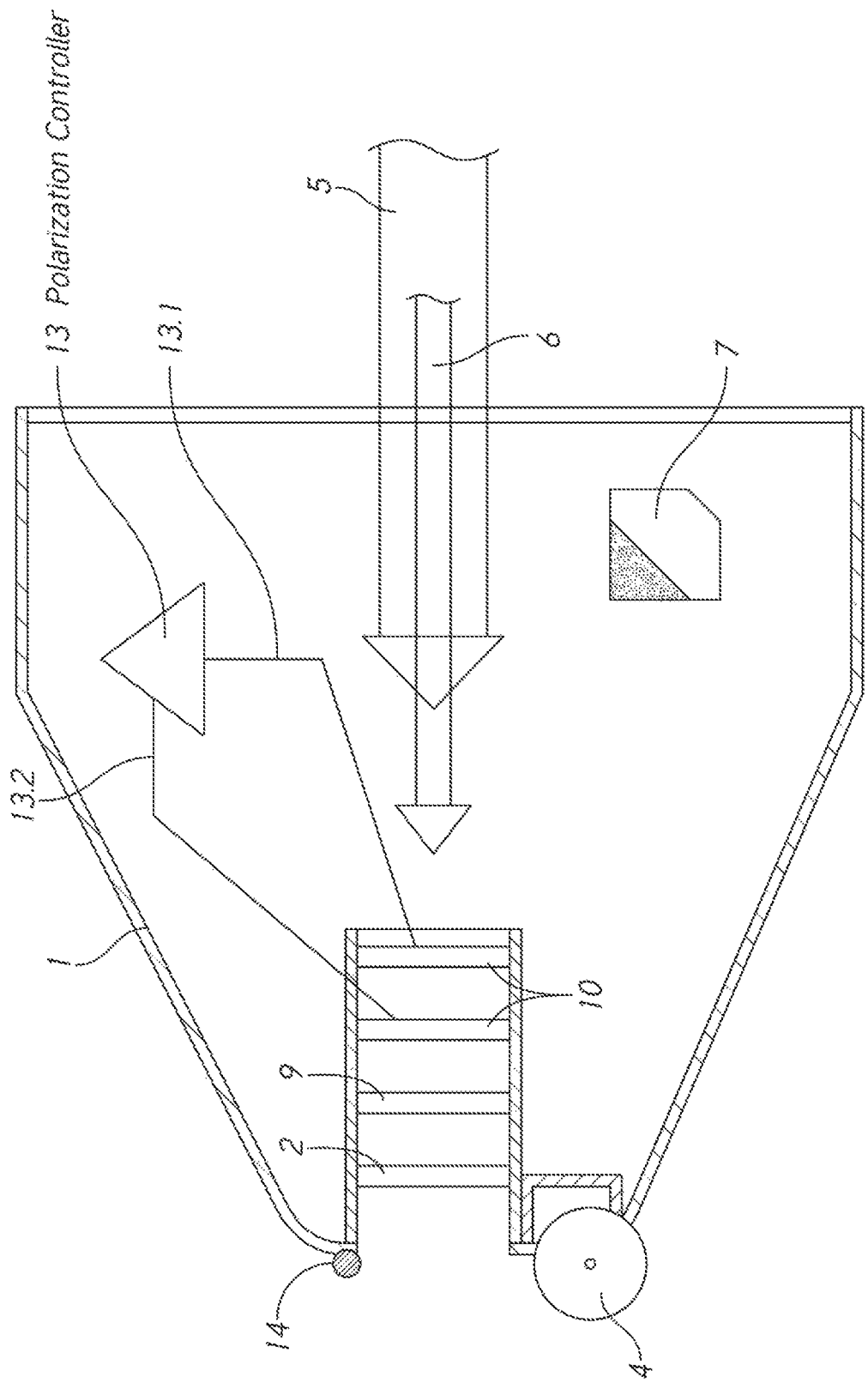
FIG. 4 is a drawing of a fourth embodiment of the tip of the invention having polarizing windows.

FIG. 4 depicts a fourth embodiment of the tip of the invention. This embodiment features a tip as shown in FIG. 1, wherein thermoelectric cooler 3, microchip connectors 8, fractional window 11, and cooling connectors 12 are omitted from the tip.

Fifth Embodiment

Figure 5:
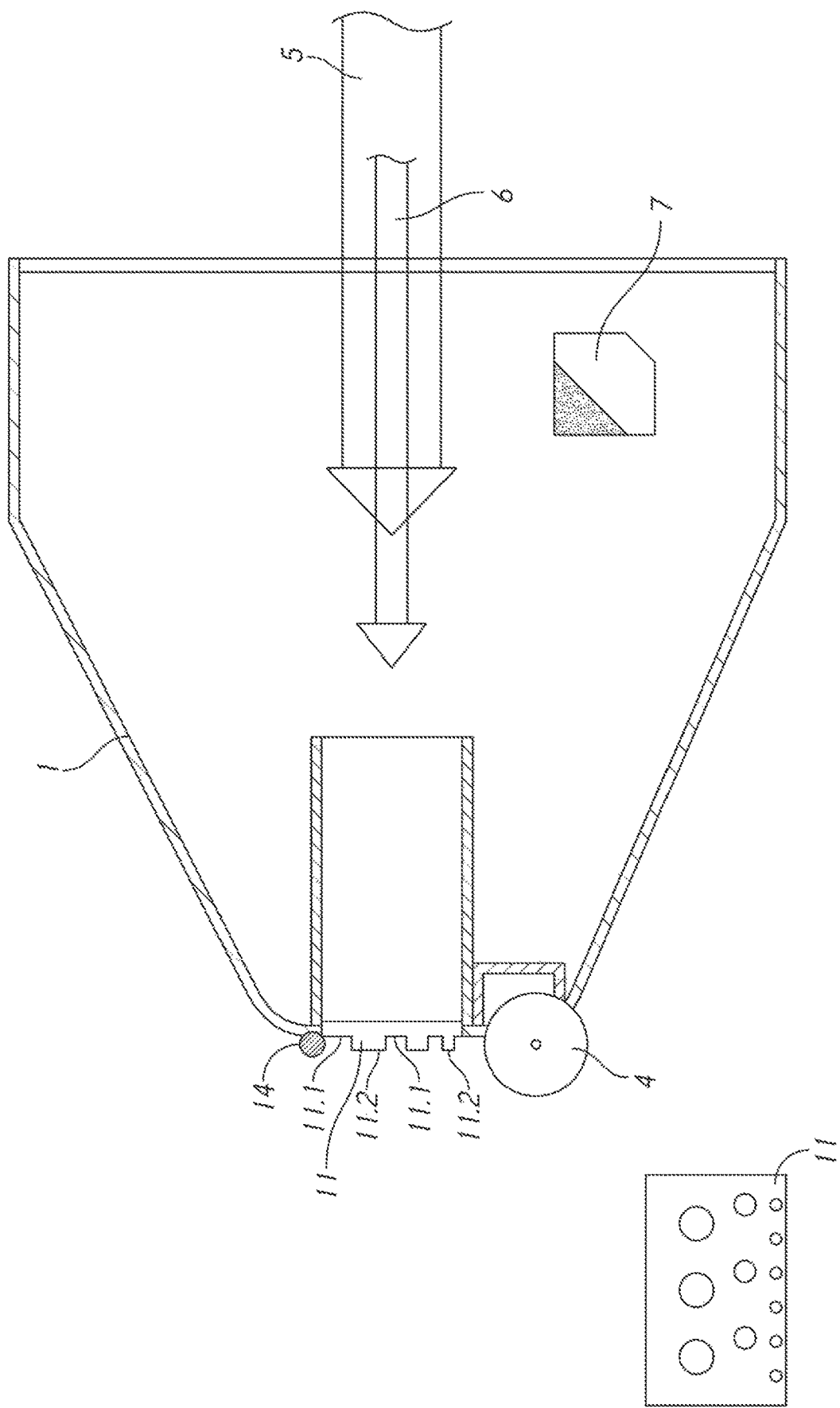
FIG. 5 is a drawing of a fifth embodiment of the tip of the invention having a fractional window.

FIG. 5 depicts a fifth embodiment of the tip of the invention. Tip 1 can contain fractional window 11 having one or more fractional depressions 11.1 surrounded by one or more planar lands 11.2 on the outward facing surface of fractional window 11. Fractional depressions 11.1 can have the same or similar shape. In some aspects of the invention, fractional depressions 11.1 and are in the shape of cylindrical columns. In other aspects, fractional depressions 11.1 are in the shape of one or more concentric rings. Fractional depressions 11.1 function to scatter, absorb and/or reflect electromagnetic beam 5 and electromagnetic beam 6 thereby splitting the beams into multiple fractions of electromagnetic energy having a modified size and shape. Thus, fractional depressions 11.1 can split one or more of electromagnetic beam 5 and electromagnetic beam 6 into a plurality of fractionated beams that are at least one of overlapping, partially overlapping, or non-overlapping beams. Planar lands 11.2 transmit electromagnetic beam 5 and electromagnetic beam 6 without modification of the beams. In at least one aspect of the invention, a fractional coating on fractional window 11 is substituted for fractional depressions 11.1. The fractional coating achieves the same function as fractional depressions 11.1 and can be made from a non-translucent material that absorbs or reflects laser light. Suitable materials for the fractional coating include, but are not limited to, evaporated metal films (e.g. aluminum and gold), silica, scandium oxide, magnesium fluoride, hafnium fluoride, or combinations thereof. The materials can be arranged in one or more layers. In at least one aspect, the fractional coating comprises a layer of silica and a layer of scandium oxide. In other aspects, the fractional coating comprises a layer of magnesium fluoride and a layer of hafnium fluoride. As with other embodiments of the tip, electromagnetic beam 5 and electromagnetic beam 6 can be laser beams. The embodiment of FIG. 5 features roller 4 and contact sensor 14 which are in communication with microchip 7 as disclosed herein.

Sixth Embodiment

Figures 6, 6A:
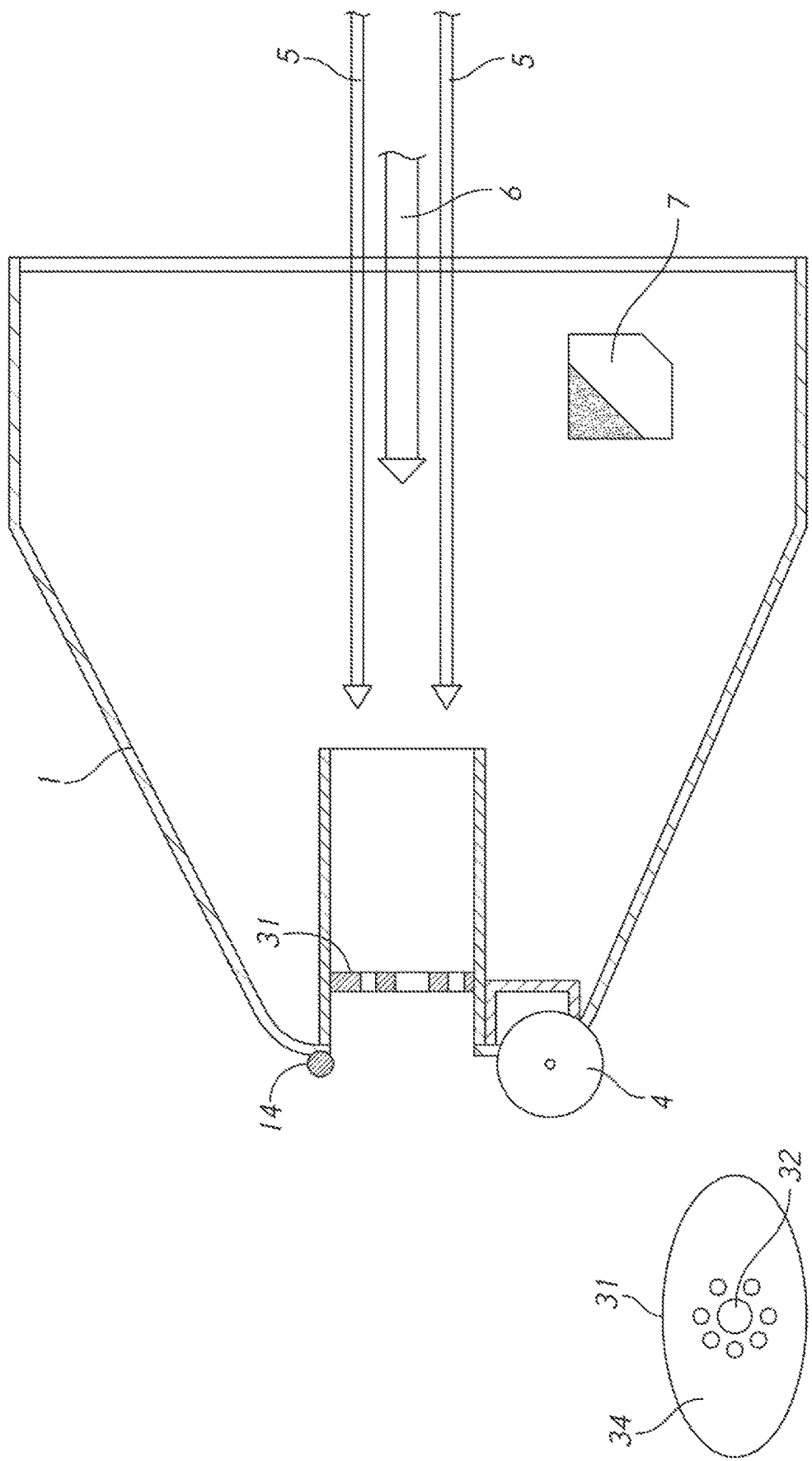
FIG. 6 shows a sixth embodiment of the tip of the invention having a beam separation window.
FIG. 6A shows a top view of the beam separation window of FIG. 6.
Figure 7:
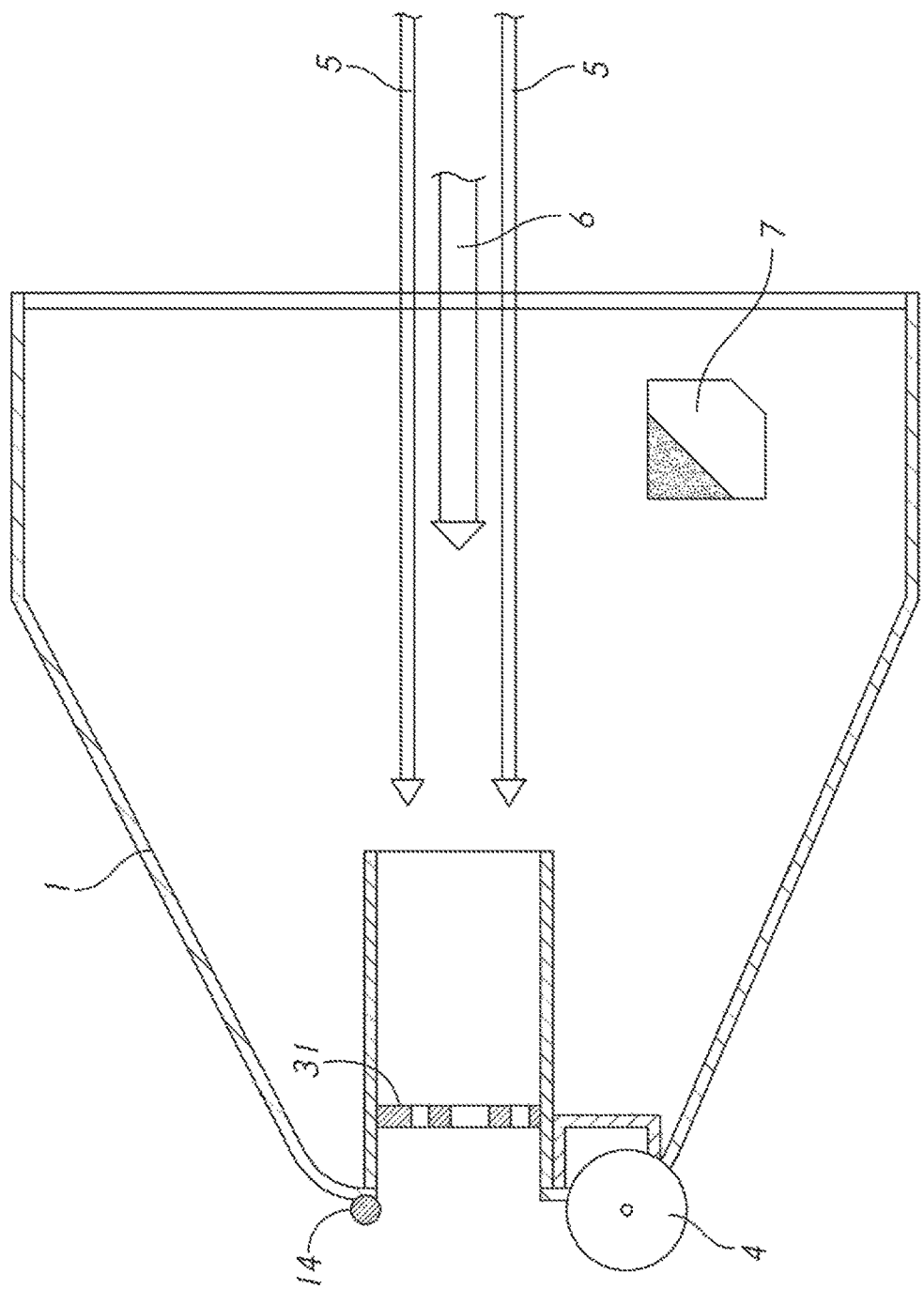
FIG. 7 shows a function of the beam separation window of the sixth embodiment of the tip of the invention.
Figure 8:
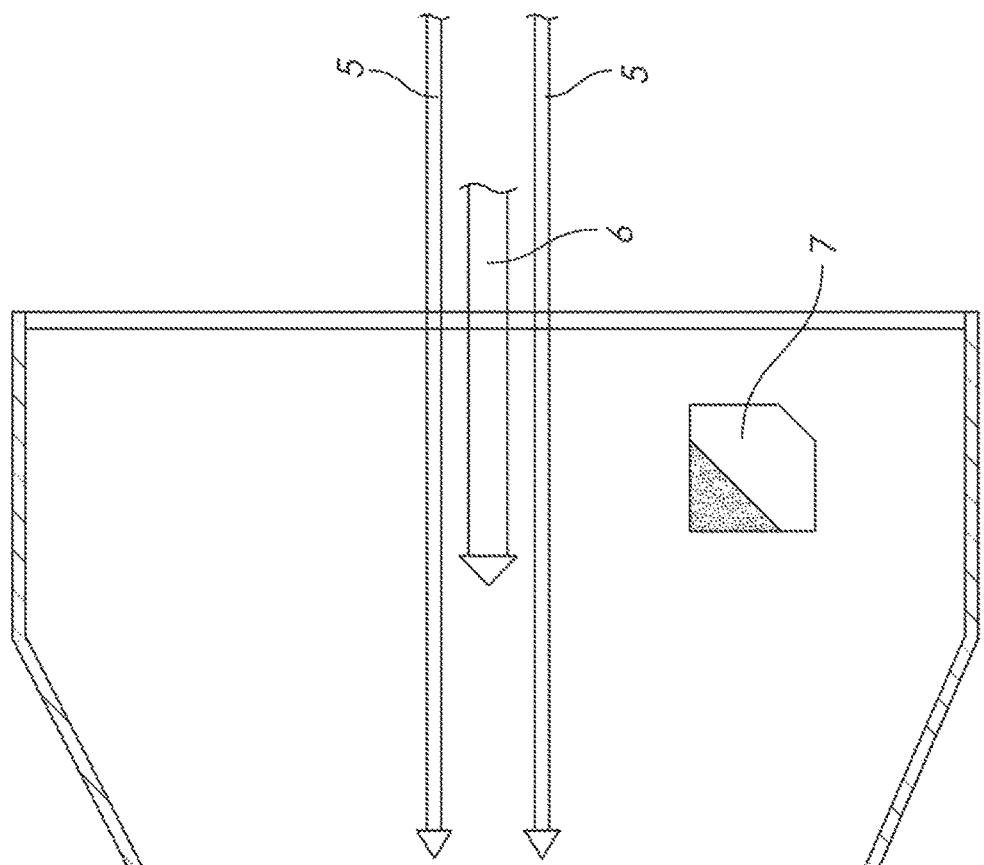
FIG. 8 shows a function of the beam separation window of the sixth embodiment of the tip of the invention.

FIGS. 6-8 depict a sixth embodiment of the tip of the invention. In this embodiment, tip 1 can have at least one beam separation window 31 housed within a column body of the same or similar material as the tip housing. Beam separation window 31 can be made of a material suitable for transmitting electromagnetic beam 5 and electromagnetic beam 6, such as sapphire, thermoconductive glass, and the like. Tip 1 can contain microchip 7 in electronic communication with roller 4 and contact sensor 14 as disclosed herein.

Beam separation window 31 comprises beam separation coating 34 on at least one planar surface of the window. Beam separation coating 34 is made of a material that selectively blocks the transmission of one or more wavelengths of electromagnetic energy through beam separation window 31, while permitting the transmission of one or more other wavelengths of electromagnetic energy. For example, beam separation coating 34 can block the transmission the wavelength of electromagnetic beam 6, while transmitting the wavelength of electromagnetic beam 5. In at least one aspect of the invention, electromagnetic beam 5 and electromagnetic beam 6 are laser beams. Electromagnetic beam 5 can be a laser beam generated by a solid state Er: YSSG laser having a wavelength of 2790 nm, and electromagnetic beam 6 can be a laser beam generated by a laser diode having a wavelength of 1,550 nm.

Beam separation coating 34 can be applied in one or more layers. Suitable materials for beam separation coating 34 include, but are not limited to, evaporated metal films (e.g. aluminum and gold), silica, scandium oxide, magnesium fluoride, hafnium fluoride, or combinations thereof. In at least one aspect of the invention, beam separation coating 34 comprises a layer of silica and a layer of scandium oxide. In other aspects, beam separation coating 34 comprises a layer of magnesium fluoride and a layer of hafnium fluoride. The materials of beam separation coating 34 can be present in one or more layers, and can have a thickness ranging between about 100 nanometers and 500 nanometers.

Figure 7A:
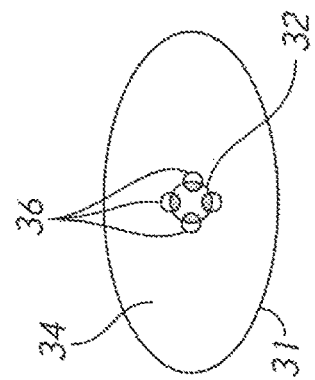
FIG. 7A shows a top view of the beam separation window of FIG. 7.
Figure 8A:
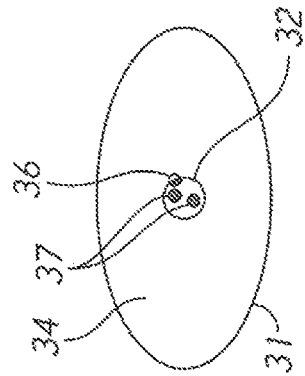
FIG. 8A shows a top view of the beam separation window of FIG. 8.

FIGS. 6A, 7A, and 8A show that beam separation window 31 can have central opening 32 which lacks beam separation coating 34 such that central opening 32 permits beam separation window 31 to transmit electromagnetic beam 5 and electromagnetic beam 6 in a pattern of overlapping beams, partially overlapping beams, non-overlapping beams, or combinations thereof. In some aspects of the invention, central opening 32 is coated with an antireflective coating as disclosed herein. It will be appreciated that beam separation coating 34 and central opening 32 can assume other configurations, wherein beam separation coating is present on one or more regions of beam separation window 31. For example, beam separation coating 34 can occupy beam separation window as one or more oval or circular coatings.

FIG. 7 depicts the function of beam separation window 31. FIG. 7A is a top view of beam separation window 31 from FIG. 7 wherein central opening 32 permits beam separation window 31 to simultaneously transmit electromagnetic beam 5 and electromagnetic beam 6 thereby permitting the overlapping, simultaneous transmission of the beams as depicted in the dark portions of split beams 36. The light portions of split beams 36 depict the transmission of only electromagnetic beam 5 as electromagnetic beam 6 is blocked by beam separation coating 34.

FIG. 8 similarly depicts the function of beam separation window 31. FIG. 8A is a top view of beam separation window 31 from FIG. 8 and shows transmitted beams 37 which depict the simultaneous transmission of overlapping electromagnetic beam 5 and electromagnetic beam 6 through central opening 32. Split beam 36 shows a dark portion wherein electromagnetic beam 5 and electromagnetic beam 6 overlap and are transmitted simultaneously through central opening 32, while the light portion of split beam 36 depicts the selective transmission of only electromagnetic beam 5 through beam separation coating 34. That is, when electromagnetic beam 5 and electromagnetic beam 6 overlap beam separation window 31 at the edge of central opening 32, beam separation coating 34 splits the beams such that separation coating 34 transmits only electromagnetic beam 5.

Seventh Embodiment

Figure 9:
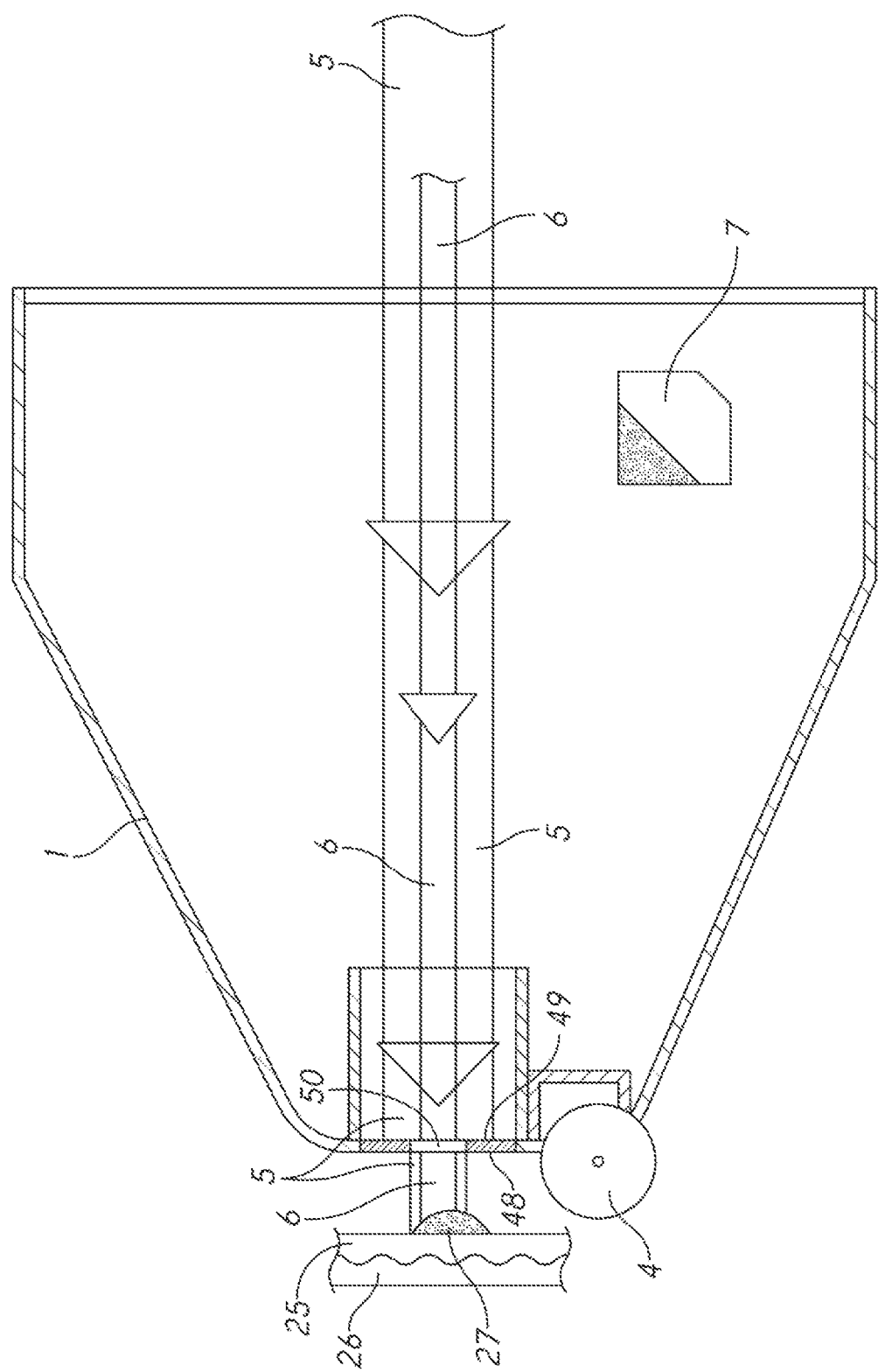
FIG. 9 shows the use of a tip of the invention in the treatment of a skin lesion with shielding of the skin surrounding the lesion.

FIG. 9 shows a seventh embodiment of the tip of the invention. In this embodiment, tip 1 comprises focusing window 48 having blocking coating 49 which surrounds focus opening 50 centrally positioned within focusing window 48. Focus opening 50 lacks blocking coating 49. Focusing window 48 can be made of sapphire, thermoconductive glass, or other material suitable for conducting electromagnetic energy, such as laser energy. Blocking coating 49 can be on at least one of the planar surfaces of focusing window 48. Blocking coating 49 is a material that prevents the transmission of electromagnetic beam 5 and electromagnetic beam 6 through focusing window 48. Blocking coating 49 can be applied in one or more layers of a material capable of blocking one or more wavelengths of electromagnetic energy. Suitable materials include, but are not limited to, magnesium fluoride, yttrium oxide, silica, aluminum oxide, cerium fluoride, hafnium fluoride, or combinations thereof. In at least one aspect of the invention, blocking coating 49 comprises a layer of magnesium fluoride and a layer of yttrium oxide. In other aspects, blocking coating 49 comprises a layer of silica and a layer of scandium oxide. Blocking coating 49 can have a thickness ranging between about 100 nanometers and about 500 nanometers.

In at least one aspect of the invention, blocking coating 49 prevents the transmission of laser energy through focusing window 48. Focus opening 50 can have one or more of the antireflective coatings disclosed herein. The antireflective coatings can be on at least one planar surface of focusing window 48. For example, focusing window 48 can have a first antireflective coating on a first planar surface of focusing window 48 that enhances the transmission of the wavelength electromagnetic beam 5, and a second antireflective coating on a second planar surface of focusing window 48 that enhances the transmission of the wavelength of electromagnetic beam 6. In at least one aspect of the invention, the antireflective coatings enhance the transmission of laser energy. In some aspects, window 48 is substituted for an opening in the body of tip 1 having a size that is the same as focus opening 50.

FIG. 9 depicts the use of tip 1 in the treatment of skin lesion 27 on the skin of a patient having epidermis 25 and dermis 26. Tip 1 transmits electromagnetic beam 5 and electromagnetic beam 6 such that the beams completely or partially overlap on skin lesion 27 while epidermis 25 and dermis 26 are shielded from the beams. In at least one aspect of the invention, electromagnetic beam 5 and electromagnetic beam 6 are laser beams and skin lesion 27 is actinic keratosis.

Eighth Embodiment

Figure 10:
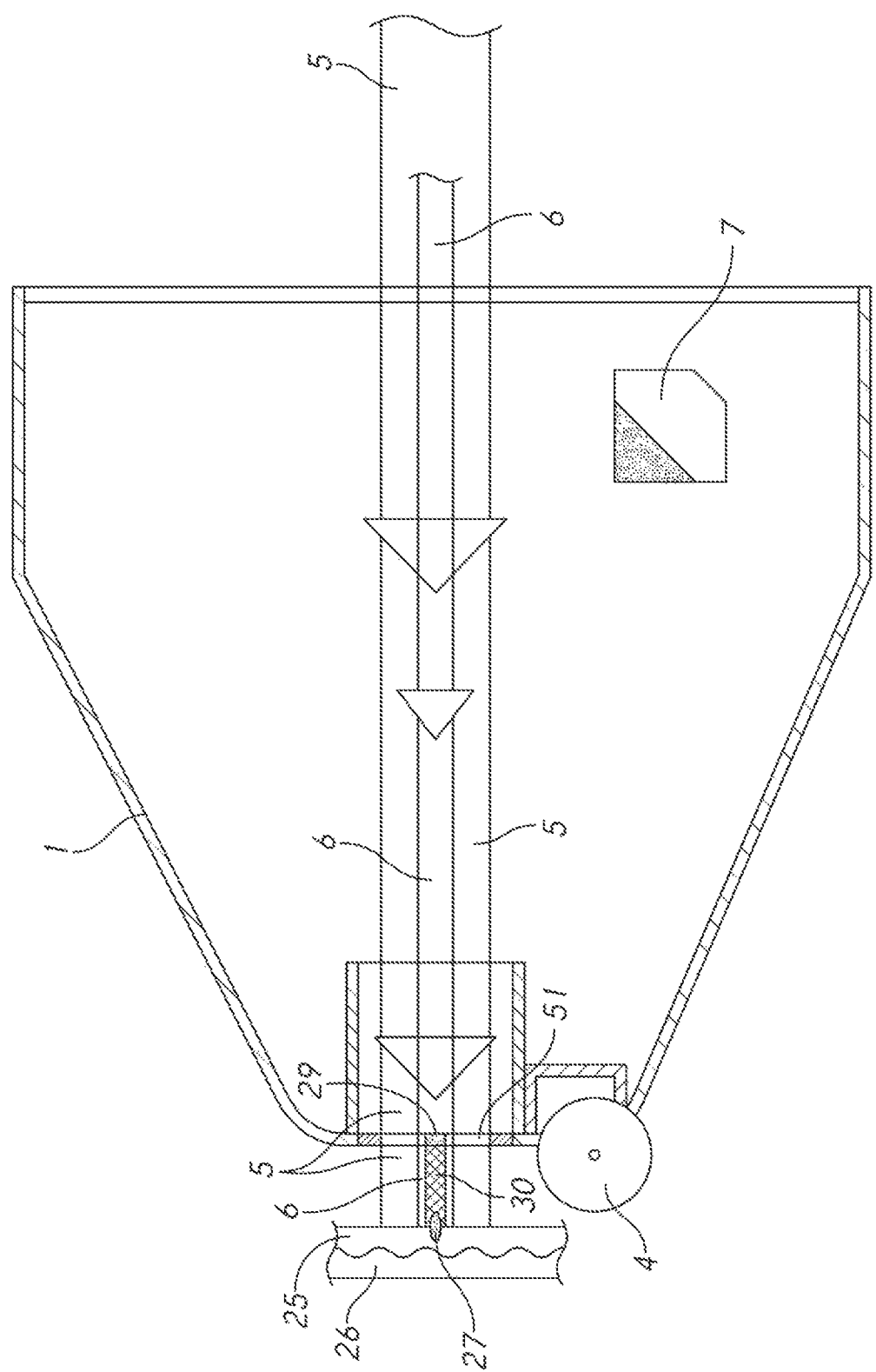
FIG. 10 shows the use of a tip of the invention in the treatment of a skin lesion with shielding applied to the skin lesion.

FIG. 10 depicts an eighth embodiment of the tip of the invention. Tip 1 comprises central blocking window 51 having blocking coating 29 centrally located within the window. Blocking window 51 can be made of a material suitable for transmitting electromagnetic beam 5 and electromagnetic beam 6. The material for blocking window 51 can be sapphire, thermoconductive glass, or other material suitable for transmitting electromagnetic energy, such as laser energy, for example. Blocking coating 29 can be on at least one of the planar surfaces of blocking window 51 and can be a material suitable for blocking electromagnetic beam 5 and electromagnetic beam 6. Suitable materials for blocking coating 29 include, but are not limited to, metal films (e.g. aluminum and gold), silica, scandium oxide, magnesium fluoride, hafnium fluoride, or combinations thereof. In one aspect, blocking coating 29 comprises a layer of magnesium fluoride and a layer of hafnium fluoride. In other aspects, blocking coating 29 comprises a layer of silica and a layer of scandium oxide. Blocking coating 29 can be present in one or more layers, and can have a thickness ranging between about 100 nanometers and about 500 nanometers. Blocking coating 29 can assume a shape that provides a desired pattern of shielding. Blocking coating 29 can be in the shape of a circle, oval, or polygon, for example. In at least one aspect of the invention, blocking coating 29 blocks laser energy.

Blocking window 51 can have one or more antireflective coatings surrounding blocking coating 29 for enhancing the transmission of at least one of electromagnetic beam 5 and electromagnetic beam 6 through blocking window 51. The antireflective coating can be one or more of the antireflective materials disclosed herein. The antireflective coatings can be on at least one of blocking window 51's planar surfaces. For example, the first planar surface of blocking window 51 can contain a first antireflective coating that enhances the transmission of the wavelength of electromagnetic beam 5, while the second opposing planar surface of shielding window 51 can contain a second antireflective coating that enhances the transmission of the wavelength of electromagnetic beam 6. The antireflective coatings can be coatings that enhance the transmission of laser energy.

FIG. 10 depicts the use of tip 1 in the treatment of skin lesion 27 on a skin having epidermis 25 and dermis 26. Tip 1 transmits electromagnetic beam 5 and electromagnetic beam 6 through shielding window 51 such that the beams completely or partially overlap on epidermis 25 and dermis 26, while skin lesion 27 is shielded from the beams by blocking coating 29 as depicted by shielded region 30 which is free of electromagnetic beam 5 and electromagnetic beam 6. In at least one aspect of the invention, electromagnetic beam 5 and electromagnetic beam 6 are laser beams and skin lesion 27 is a neoplastic lesion, such as melanoma, for example.

Electromagnetic Emitting Systems

Figure 11:
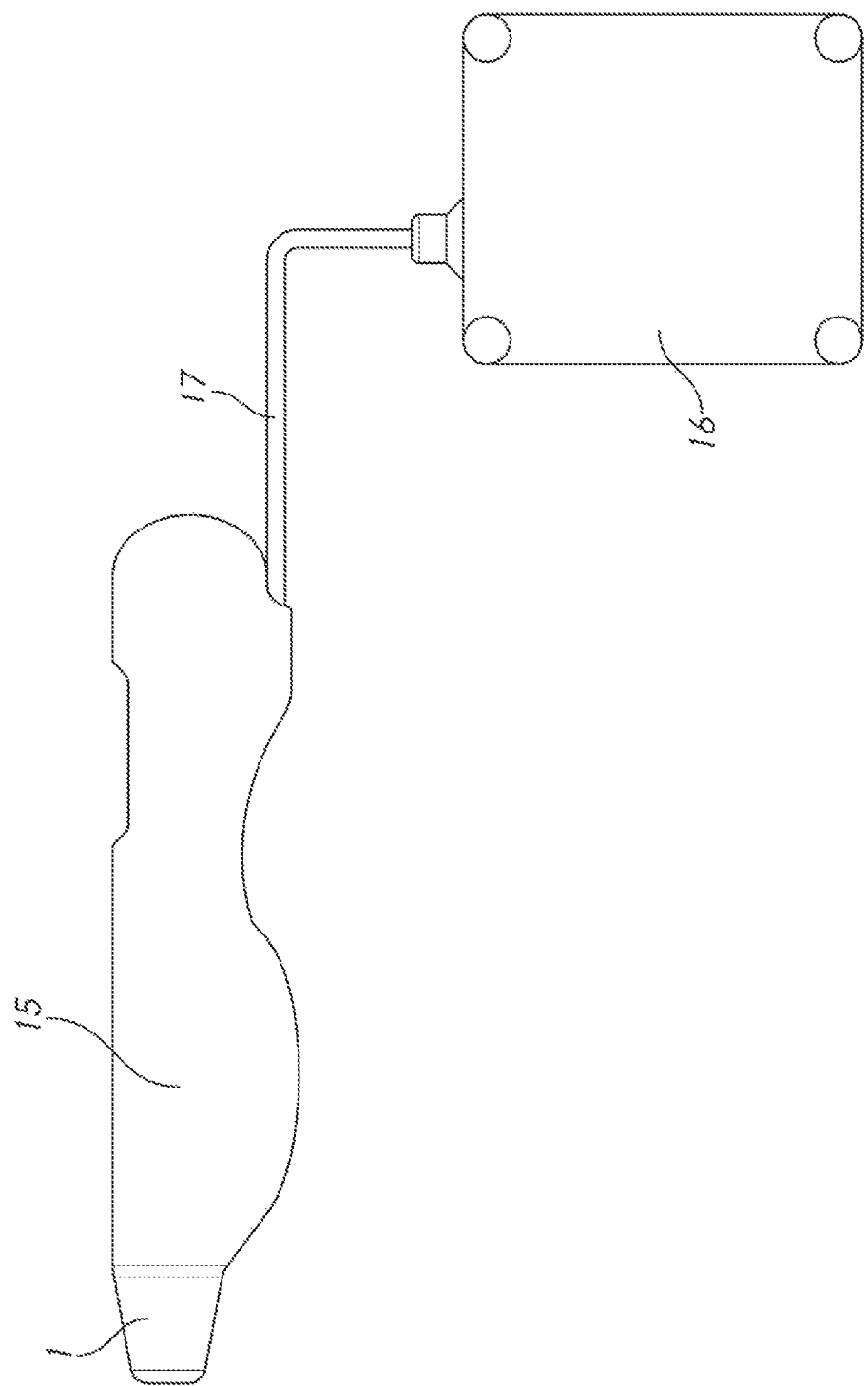
FIG. 11 shows the tip of the invention as a component of a laser treatment system.

In at least one aspect, the invention provides an electromagnetic energy emitting system comprising a tip as disclosed herein. FIG. 11 depicts a laser system comprising tip 1 and laser unit 15 which is electronically connected to power supply 16 through conducting wire 17. Tip 1 can be detachably connected to laser unit 15, or manufactured as an integral component of laser unit 15. In some aspects of the invention, laser unit 15 is a laser-generating handpiece. Power supply 16 can be a rechargeable battery or direct power supply, such as an electrical outlet. Power supply 16 can provide power to features of tip 1, such as thermoelectric cooler 3 and polarization controller 13. Thus, it will be understood that in aspects wherein tip 1 is detachably connected to laser unit 15, tip 1 can comprise electrical connectors for providing an electronic connection between tip 1 and handpiece 15.

Figure 14:
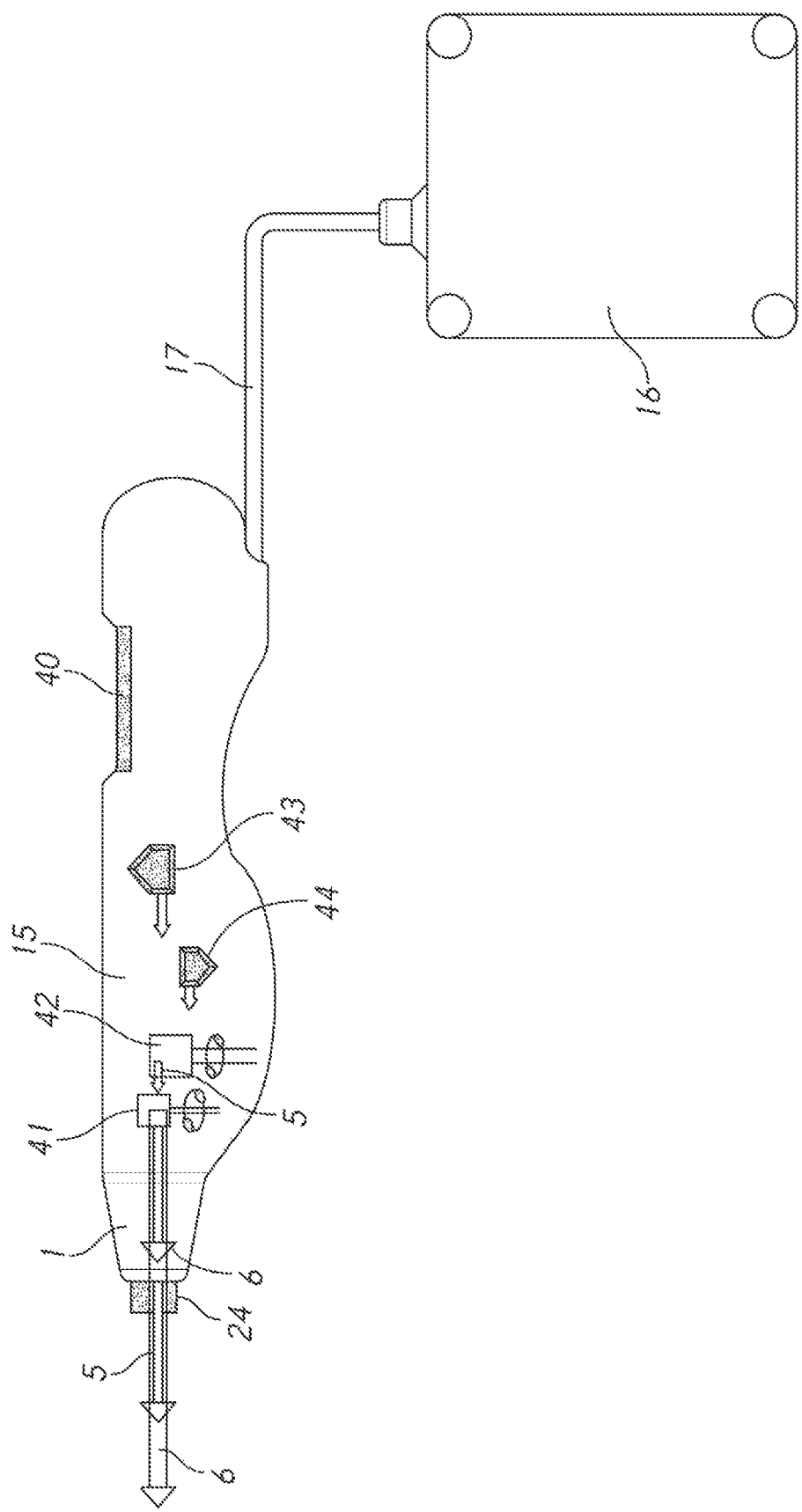
FIG. 14 shows the tip of the invention as a component of a laser treatment system that is adapted to administer IPL.

As shown in FIG. 14, laser unit 15 can comprise scanning mirror 41 for electromagnetic beam 5 and scanning mirror 42 for electromagnetic beam 6. Laser unit 15 can comprise laser emission unit 43 for generating electromagnetic beam 5 and laser emission unit 44 for generating electromagnetic beam 6. Laser unit 15 can comprise display screen 40 for displaying feedback and permitting a user to control the operation of laser unit 15. Display screen 40 can display and permit the user to control the mode of the lasers, the number of pulses delivered, the distance between irradiated spots on the surface being treated, the total combined energy delivered in a treatment application, and the energy level of each pulse for each wavelength. It will be understood that display screen 40 can be in communication with at least one of microchip 7 and a processor within laser unit 15 that collects operating information and receives instructions through display screen 40. Tip 1 can comprise ultrasound transducer 24 which is adapted to produce ultrasound on the tissue being treated, such as the skin of a patient, for example. It will be understood that ultrasound transducer 24 can be in electronic communication with microchip 7 and can be electronically coupled to power supply 16.

Figure 12:
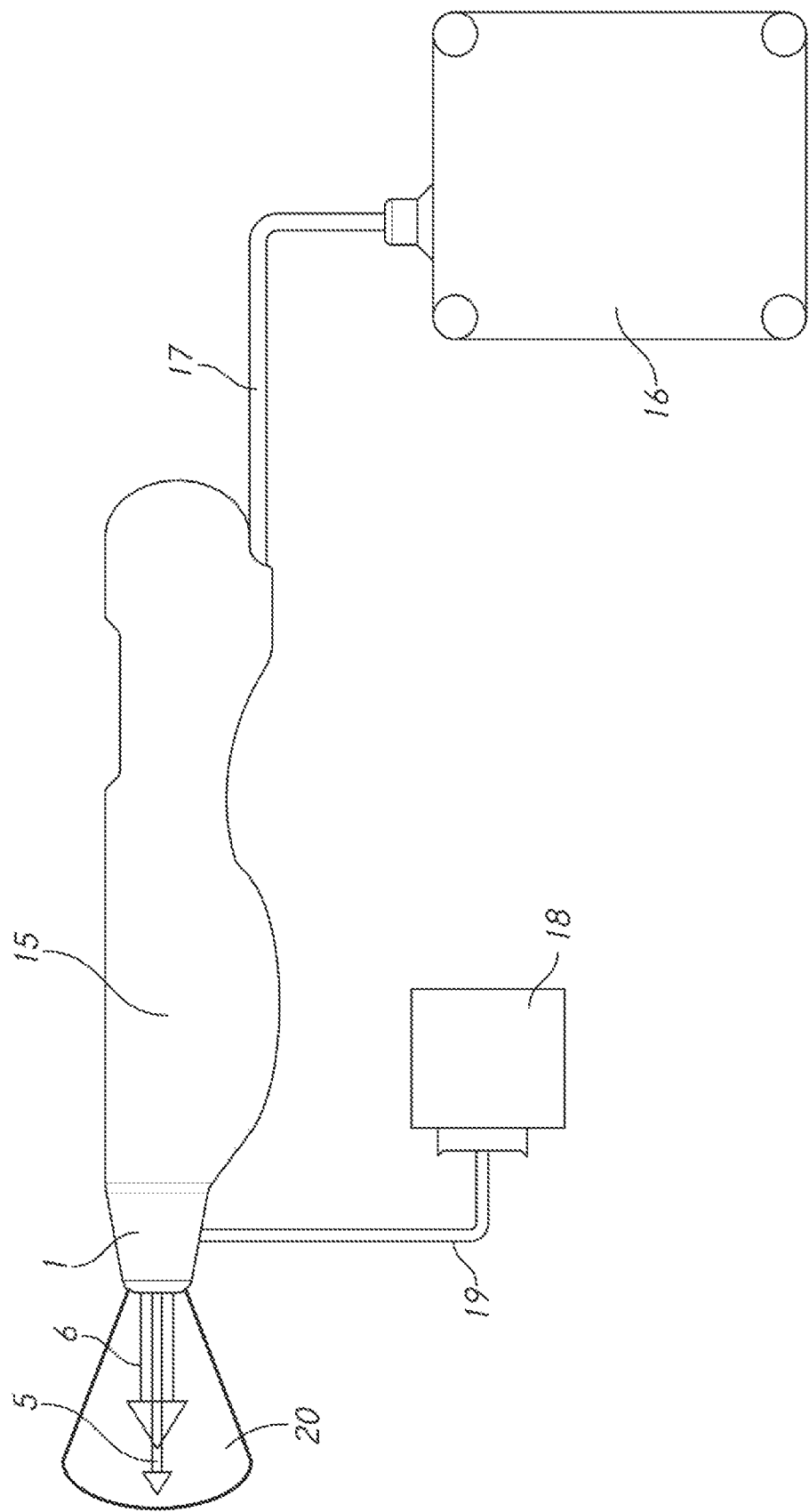
FIG. 12 shows the tip of the invention as a component of a laser treatment system that is adapted to administer ultrasound energy.

FIG. 12 depicts a laser treatment system wherein tip 1 is in electronic communication with magnetron 18 through microwave conductor 19 such that laser unit 15 is adapted to activate tip 1 to simultaneously administer radiofrequency 20, electromagnetic beam 5, and electromagnetic beam 6 onto a tissue to be treated, such as the skin of a patient, for example. In at least one aspect of the invention, electromagnetic beam 5 and electromagnetic beam 6 are laser beams.

Figure 13:
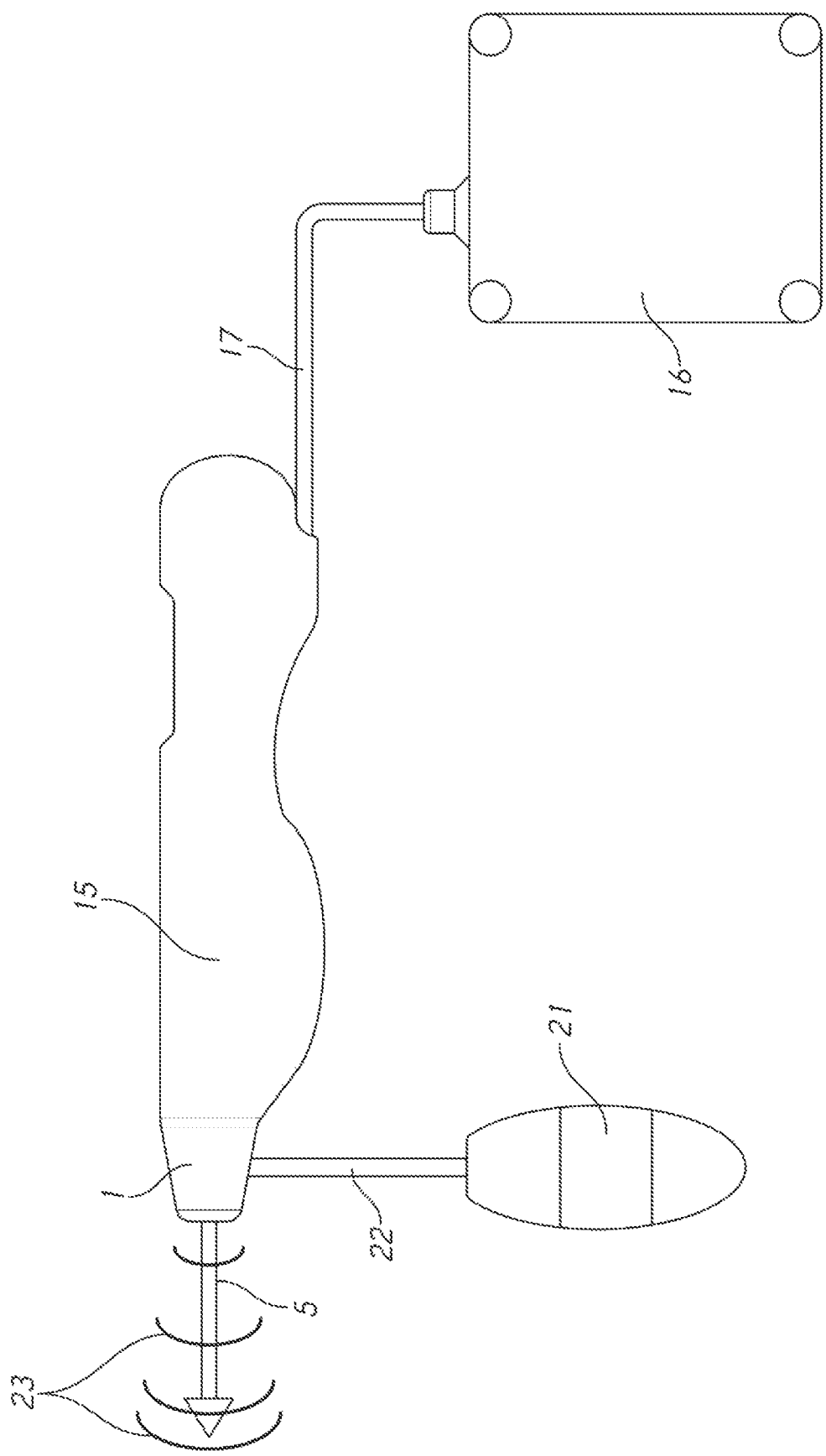
FIG. 13 shows the tip of the invention as a component of a laser treatment system that is adapted to administer microwave energy.

FIG. 13 depicts a laser treatment system wherein tip 1 and laser unit 15 are in electronic communication with IPL source 21 through fiber optic conductor 22 such that laser unit 15 is adapted to administer non-coherent light 23 from IPL source 21 together with laser energy onto a treated tissue, such as the skin of a patient. In some aspects of the invention, tip 1 comprises at least one LED light source adapted to illuminate the tissue of the patient through activation of laser unit 15.

Laser units for use with the tip of the invention can be any laser unit capable of treating a skin condition. Suitable laser units include, but are not limited to laser units produced by Dolleris Technology™ of Vancouver, Canada, Intezity Innovation™ of Hvidovre, Denmark, nLight™, of Vancouver, Canada, Coherent™ of Santa Clara, Calif., IPG Photonics™ of Oxford, Mass., Palomar Cynosure™ of Westford, Mass., Candela™ of Wayland, Mass., Sciton™ of Palo Alto, Calif., Lumenis™ of Santa Clara, Calif., Cutera™ of Brisbane, Calif., Lutronic™ of Freemont, Calif., and Aerolase™ of Tarrytown, N.Y.

Method of Treatment

In at least one embodiment, the invention provides a method for treating a skin condition on a patient in need thereof. The method can be practiced by providing tip 1, attaching tip 1 to an electromagnetic energy emitting system, contacting tip 1 with the skin of a patient having a skin condition in need of treatment, activating the electromagnetic energy emitting system to produce at least two beams of electromagnetic energy having the same or different wavelengths, wherein activating the electromagnetic energy emitting system projects the electromagnetic beams into tip 1 whereupon tip 1 produces a pattern of electromagnetic energy on the skin, wherein the pattern comprises overlapping beams, partially overlapping beams, non-overlapping beams, or combinations thereof. In at least one aspect of the invention, the electromagnetic energy emitting system is laser unit 15 that emits laser beams.

The method can be practiced by providing tip 1 as disclosed herein and attaching tip 1 to laser unit 15 that emits electromagnetic beam 5 and electromagnetic beam 6 as laser beams. The laser beams can be emitted in at least one of pulse beam and continuous beam mode. Tip 1 is contacted with the skin of a patient causing contact sensor 14 to send a signal to microchip 7. The signal is processed by microchip 7 causing microchip 7 to enable laser unit 15 to be activated for the emission of laser beam 5 and laser beam 6 through tip 1. Upon activation of laser unit 15 by a user, laser beam 5 and laser beam 6 are emitted from laser unit 15 into tip 1 whereupon tip 1 emits laser beams 5 and laser beam 6 as at least one of overlapping, partially overlapping, and non-overlapping beams thereby treating the skin of the patient. The tip can optionally contain roller 4 in electronic communication with the microchip such that moving tip 1 across the skin of the patient rotates roller 4 sending a signal to microchip 7 which activates laser unit 15 to emit laser beam 5 and laser beam 6 through tip 1 and onto the skin of the patient.

Tip 1 can optionally contain one or more polarizing windows 10 that function to modulate the temporal shape of electromagnetic beam 5 and electromagnetic beam 6 making the leading edge of the beams more intense and the remaining pulse less intense to achieve thermal post conditioning of the treated tissue. Alternatively, polarization windows 10 can be adapted to shape the electromagnetic beams such that the beginning of the pulses starts at a low intensity to achieve pre-heating, and the end of the pulses finish with a more intense energy. In at least one aspect of the invention, the electromagnetic beams are laser beams.

Tip 1 can optionally contain fractional window 11 that is adapted to scatter, absorb and/or reflect electromagnetic beam 5 and electromagnetic beam 6 as they are emitted from tip 1 such that the tip treats the tissue with multiple fractions of electromagnetic energy having a modified size and shape. Tip 1 can optionally contain thermoelectric cooler 3 that cools at least one of transmitting windows 2 and 9, and polarizing windows 10 so that the tip can be safely contacted with the skin of a patient without burning the skin or causing discomfort to the patient. Thermoelectric cooler 3 can be a Peltier cooling module.

In at least one aspect of the method, tip 1 and laser unit 15 are used to treat a skin condition selected from wrinkles, loss of skin elasticity, scars, rhytides, acne, telangiectasia, pigmented lesions, and combinations thereof. Tip 1 and laser unit 15 can be used to treat wrinkles and loss of skin elasticity, wherein laser unit 15 emits a first one or more laser beams having a wavelength of 1550 nm, and a second one or more laser beams having a wavelength of 1930 nm. Tip 1 and laser unit 15 can be used to treat at least one of acne and acne scar tissue, wherein laser unit 15 emits a first one or more laser beams having a wavelength of 1550 nm, and a second one or more laser beams having a wavelength of 1930 nm. Tip 1 and laser unit 15 can be used to treat a skin condition selected from rhytides, scars, wrinkles, loss of skin elasticity, and combinations thereof, wherein the laser unit emits a first one or more laser beams having a wavelength of 980 nm, a second one or more laser beams having a wavelength of 1440 nm, and a third one or more laser beams having a wavelength of 1930 nm. Tip 1 and laser unit 15 can be used to treat a skin condition selected from telangiectasia, pigmented lesions, and a combination thereof, wherein laser unit 15 emits a first one or more laser beams having a wavelength of 532 nm, a second one or more laser beams having a wavelength of 540 nm, and a third one or more laser beams having a wavelength of 980 nm. Laser unit 15 can generate the laser beams from a plurality of laser diodes operating in pulse mode. In some aspects of the method invention, the tip is used to deliver one or more therapeutic or cosmetic agents. In such aspects, the tip and electromagnetic energy system are used to treat the skin of a patient, and the agents are delivered to the treated skin. Suitable agents for use with the method include, but are not limited to, those agents disclosed in U.S. Pat. No. 10,206,743 and US Patent Application Publication No. 2017/0225010, the entire contents of which are incorporated herein by reference for all purposes.

The reader should understand that the above specific embodiments of the present invention are merely examples and that many changes and modifications could be made without departing from the important concepts of simultaneous multiwavelength, multibeam, multimode electromagnetic energy delivery of the present invention.

While illustrative embodiments of the invention have been described herein, the present invention is not limited to the various preferred embodiments described herein, but includes any and all embodiments having equivalent elements, modifications, omissions, combinations (e.g. of aspects across various embodiments), adaptations and/or alterations as would be appreciated by those in the art based on the present disclosure. The limitations in the claims are to be interpreted broadly based on the language employed in the claims and not limited to the examples described in the present specification or during prosecution of the application, which examples are to be construed as non-exclusive.

The invention claimed is:

1. A tip for transmitting therapeutic electromagnetic energy, comprising:
   a) a tip body; and
   b) at least one window, wherein said at least one window comprises a coating adapted to (i) transmit a first one or more beams of electromagnetic energy having a first wavelength, and (ii) at least one of block and partially block a second one or more beams of electromagnetic energy having a second wavelength, wherein said coating comprises at least one opening that is adapted to permit said second one or more beams of electromagnetic energy to traverse said at least one window without obstruction;
   d) wherein said coating and said at least one opening cooperate to simultaneously transmit said first one or more beams of electromagnetic energy and said second one or more beams of electromagnetic energy onto a tissue in a pattern comprising non-overlapping beams, and at least one of overlapping beams and partially overlapping beams.

2. The tip of claim 1, wherein said coating is adapted to transmit laser energy, coherent light, non-coherent light, microwave energy, ultraviolet energy, intense pulsed light, radiofrequency energy, or combinations thereof.

3. The tip of claim 1, wherein said coating is adapted to transmit wavelengths of laser energy selected from about 540 nm, about 700 nm, about 980 nm, about 1064 nm, about 1440 nm, about 1300 nm, about 1450 nm, about 1550 nm, about 1930 nm, about 2790 nm, about 2790 nm, about 2940 nm, about 10600 nm, and combinations thereof.

4. The tip of claim 1, wherein said coating is adapted to transmit laser energy in at least one of pulse mode and continuous mode.

5. The tip of claim 1, wherein said tip comprises at least one polarizing window.

6. The tip of claim 1, wherein said tip comprises a thermoelectric cooler.

7. The tip of claim 6, wherein said thermoelectric cooler is a Peltier cooling module.

8. The tip of claim 1, wherein said tip comprises an ultrasound transducer.

9. The tip of claim 1, wherein said tip is in communication with a magnetron.

10. The tip of claim 1, wherein said tip is in communication with an intense pulsed light source.

11. The tip of claim 1, wherein said tip is connected to an electromagnetic energy emitting system adapted to emit said first one or more beams of electromagnetic energy and said second one or more beams of electromagnetic energy.

12. The tip of claim 11, wherein said electromagnetic energy emitting system is selected from a laser system, a coherent light system, non-coherent light system, intense pulsed light system, light emitting diode system, microwave system, and combinations thereof.

13. The tip of claim 12, wherein said laser system is selected from a solid-state laser system, laser diode system, gas laser system, chemical laser system, dye laser system, metal-vapor laser system, semiconductor laser system, and combinations thereof.

14. The tip of claim 13, wherein said laser system is adapted to deliver said first one or more beams of electromagnetic energy and said second one or more beams of electromagnetic energy in at least one of pulse mode and continuous mode.

15. The tip of claim 11, wherein said tip is adapted to detachably connect to said electromagnetic energy emitting system.

16. A tip for delivering therapeutic electromagnetic energy, comprising:
    a) a tip body; and
    b) a beam separation window having at least one coating that is adapted to (i) transmit a first beam of electromagnetic energy having a first wavelength, and (ii) at least one of block and partially block a second beam of electromagnetic energy having a second wavelength;
    d) wherein said at least one coating has at least one opening that is adapted to transmit said second beam of electromagnetic energy without obstruction;
    e) wherein said at least one coating and said at least one opening cooperate to simultaneously transmit said first beam of electromagnetic energy and said second beam of electromagnetic energy onto a tissue in a pattern comprising non-overlapping beams and at least one of overlapping beams and partially overlapping beams.

17. The tip of claim 16, wherein said at least one coating comprises a plurality of said at least one opening.

18. The tip of claim 16, wherein said at least one opening comprises an antireflective coating.

19. The tip of claim 16, wherein said at least one coating comprises a plurality of layers.

20. The tip of claim 16, wherein said at least one coating is adapted to block or partially block laser energy.

21. The tip of claim 16, wherein said at least one coating is selected from an evaporated metal film, silica, scandium oxide, magnesium fluoride, hafnium fluoride, and combinations thereof.

22. A method for treating a skin condition, comprising:
    a) providing an electromagnetic energy emitting system having a tip according to claim 1; and
    b) activating said system to emit two or more beams of electromagnetic energy through said tip and onto the skin of a patient in need of treatment of a skin condition;
    c) wherein activating said system treats said skin condition by simultaneously emitting said two or more beams of electromagnetic energy onto said skin in a pattern comprising non-overlapping beams and at least one of overlapping beams and partially overlapping beams.

23. The method of claim 22, wherein said two or more beams of electromagnetic energy comprise energy selected from laser energy, coherent light energy, non-coherent light energy, intense pulsed light energy, microwave energy, radiofrequency, and combinations thereof.

24. The method of claim 23, wherein said laser energy is generated by a solid-state laser system, laser diode system, gas laser system, chemical laser system, dye laser system, metal-vapor laser system, semiconductor laser system, or combinations thereof.

25. The method of claim 23, wherein said laser energy has a wavelength selected from about 540 nm, about 700 nm, about 980 nm, about 1064 nm, about 1440 nm, about 1300 nm, about 1450 nm, about 1550 nm, about 1930 nm, about 2790 nm, about 2790 nm, about 2940 nm, about 10600 nm, and combinations thereof.

26. The method of claim 23, wherein said laser energy is emitted in at least one of pulse mode and continuous mode.

27. The method of claim 22, wherein said tip polarizes said two or more beams of electromagnetic energy onto said skin of said patient.

28. The method of claim 22, wherein said tip blocks at least a portion of one or more of said two or more beams of electromagnetic energy.

29. The method of claim 22, wherein activating said system applies ultrasound energy to said skin.

30. The method of claim 22, wherein activating said system applies microwave energy to said skin.

31. The method of claim 22, wherein activating said system applies intense pulsed light to said skin.

32. The method of claim 22, wherein said skin condition is selected from wrinkles, loss of skin elasticity, scars, rhytides, acne, telangiectasia, vitiligo, pigmented lesions, tattoo removal, skin lesions, and combinations thereof.

* * * * *